US012791561B2

(12) United States Patent
Chang et al.

(10) Patent No.: US 12,791,561 B2
(45) Date of Patent: Nov. 10, 2026

(54) LOW AFFINITY RED FLUORESCENT INDICATORS FOR IMAGING $CA^{2+}$ IN EXCITABLE AND NONEXCITABLE CELLS

(71) Applicants: THE GOVERNORS OF THE UNIVERSITY OF ALBERTA, Edmonton (CA); THE CHANCELLOR MASTERS AND SCHOLARS OF THE UNIVERSITY OF OXFORD, Oxfordshire (GB)

(72) Inventors: Yu-Fen Chang, Edmonton (CA); Jiahui Wu, Edmonton (CA); Matthew J. Daniels, Edmonton (CA); Robert E. Campbell, Edmonton (CA)

( * ) Notice: Subject to any disclaimer, the term of this patent is extended or adjusted under 35 U.S.C. 154(b) by 1423 days.

(21) Appl. No.: 16/977,396

(22) PCT Filed: Mar. 1, 2019

(86) PCT No.: PCT/CA2019/050254
§ 371 (c)(1),
(2) Date: Sep. 1, 2020

(87) PCT Pub. No.: WO2019/165563
PCT Pub. Date: Sep. 6, 2019

(65) Prior Publication Data

US 2021/0063404 A1 Mar. 4, 2021

Related U.S. Application Data

(60) Provisional application No. 62/637,808, filed on Mar. 2, 2018.

(51) Int. Cl.

| | |
|---|---|
| ***G01N 33/58*** | (2006.01) |
| ***C07K 14/47*** | (2006.01) |
| ***G01N 21/64*** | (2006.01) |

(52) U.S. Cl.
CPC ....... *G01N 33/582* (2013.01); *C07K 14/4728* (2013.01); *G01N 21/6428* (2013.01);
(Continued)

(58) Field of Classification Search
CPC ............. G01N 33/582; G01N 21/6428; G01N 21/6456; G01N 2021/6439; C07K 14/4728; C07K 2319/60
See application file for complete search history.

(56) References Cited

FOREIGN PATENT DOCUMENTS

| | | |
|---|---|---|
| JP | 2013239938 | 11/2013 |
| WO | 2012097150 | 7/2012 |

(Continued)

OTHER PUBLICATIONS

Akerboom, J. et al. (2013) 4I2Y: Crystal Structure of the genetically encoded calcium indicator RGECO1. Protein Data Bank. Retrieved from: <rcsb.org/structure/4I2Y>. Accessed on: Oct. 18, 2024. (Year: 2013).*

(Continued)

*Primary Examiner* — Samira J Jean-Louis
*Assistant Examiner* — Bailey M Morgan
(74) *Attorney, Agent, or Firm* — Bennett Jones LLP

(57) ABSTRACT

The present disclosure relates to genetically encoded low affinity, fluorescent $Ca^{2+}$ indicators, which may be targeted to endoplasmic reticulum, the sarcoplasmic reticulum and/or the mitochondria. It also relates to polynucleotides, vectors and host cells which encode or include such low affinity $Ca^{2+}$ indicators, and methods of detecting $Ca^{2+}$ levels in a cell using such indicators.

3 Claims, 15 Drawing Sheets

Specification includes a Sequence Listing.

(52) U.S. Cl.
CPC ..... *G01N 21/6456* (2013.01); *C07K 2319/60* (2013.01); *G01N 2021/6439* (2013.01)

(56) References Cited

FOREIGN PATENT DOCUMENTS

| | | |
|---|---|---|
| WO | 2017048808 | 3/2017 |
| WO | 2018075623 | 4/2018 |
| WO | 2019014072 | 1/2019 |

OTHER PUBLICATIONS

Campbell, Robert. CMV-ER-LAR-GECO1 (Plasmid #61244). Retrieved from: <addgene.org/61244>. Accessed on Oct. 9, 2024. (Year: 2014).*
Iino, Masamitsu. pCMV R-CEPIA1er (Plasmid #58216). Retrieved from: <addgene.org/58216/>. Accessed on Oct. 16, 2024. (Year: 2014).*
Suzuki, J. et al. (2014). Imaging intraorganellar Ca2+ at subcellular resolution using CEPIA. Nat. Commun. 5:4153. (Year: 2014).*
Wu, J., Development of red fluorescent protein-based calcium ion and glutamate indicators, thesis, Jan. 1, 2014, Department of Chemistry, University of Alberta, Edmonton, Alberta, Canada. (Year: 2014).*
Kim and Hwang. (2013). "Direct Targeting of Proteins from the Cytosol to Organelles: The ER versus Endosymbiotic Organelles." Traffic, 14(6):613-621. (Year: 2013).*
Kosugi et al. (2009). "Six Classes of Nuclear Localization Signals Specific to Different Binding Grooves of Importin alpha*" J. Biol. Chem., 284(1):478-485. (Year: 2009).*
Wu, "Development of red fluorescent protein-based calcium ion and glutamate indicators" (2014).
Wu et al, "Red fluorescent genetically encoded Ca2+ indicators for use in mitochondria and endoplasmic reticulum" Biochem J, Nov. 15, 2014, vol. 264, pp. 13-22.
Wu et al, "Improved orange and red Ca2+ indicators and photophysical considerations for optogenetic applications" ACS Chem Neurosci, 2013, vol. 4, pp. 963-972.
Lian et al, "Directed cardiomyocyte differentiation from human pluripotent stem cells by modulating Wnt/B-catenin signaling under fully defined conditions" Nat Protoc, 2013, vol. 8, pp. 162-175.
Wu et al, "A long stokes shift red fluorescent Ca2+ indicator protein for two-photon and ratiometric imaging" Nat Commun, 2014, vol. 5(5262), pp. 1-11.
Miyawaki A. and Niino Y., Molecular Spies for Bioimaging-Fluorescent Protein-Based Probes, Molecular Cell Review, May 21, 2015, pp. 632-643, vol. 58, No. 4.
Suzuki J. et al., Imaging intraorganellar Ca2+ at subcellular resolution using CEPIA, Nature Communications, Jun. 13, 2014, vol. 5, No. 1., doi: 10.1038/ncomms5153.
Wu, J., Development of red fluorescent protein-based calcium ion and glutamate indicators, thesis, Jan. 1, 2014, pp. 1-98, Department of Chemistry, University of Alberta, Edmonton, Alberta, Canada.
Extended European Search Report, Aug. 11, 2021.

* cited by examiner

LOW AFFINITY RED FLUORESCENT INDICATORS FOR IMAGING $CA^{2+}$ IN EXCITABLE AND NONEXCITABLE CELLS

SEQUENCE LISTING INCORPORATION PARAGRAPH

The Sequence Listing associated with this application is filed in electronic format via e-PCT and hereby incorporated by reference into the specification in its entirety. The name of the text file containing the Sequence Listing is "pctca2019050254-seql.txt". The size of the text file is 48,741 bytes and the text file was created on Mar. 1, 2019.

FIELD

This invention relates generally to low-affinity, fluorescent $Ca^{2+}$ indicators, which may be targeted to the endoplasmic reticulum, the sarcoplasmic reticulum and/or the mitochondria.

BACKGROUND

In heart cells, the sarcoplasmic reticulum (SR) is responsible for amplification of $Ca^{2+}$ induced $Ca^{2+}$ release (CICR), which enables voltage dependent $Ca^{2+}$ entry triggering myofilament contraction. As contraction is associated with motion of the SR, ratiometric (as opposed to intensiometric) imaging approaches are necessary to correct for movement artefacts.

Sub-cellular compartments such as the mitochondria, the endoplasmic reticulum (ER), and the SR, have calcium ion ($Ca^{2+}$) concentrations ranges spanning from low micromolar to high millimolar. In compartments with high $Ca^{2+}$ concentrations, fluorescent indicators which are optimized for the detection of cytoplasmic $Ca^{2+}$ (typically in the 0.1 to 10 UM range) become saturated and unresponsive to physiologically relevant changes in $Ca^{2+}$ concentration. To address this problem, substantial research effort has gone into developing low affinity $Ca^{2+}$ indicators, including genetically-encoded fluorescent proteins (FP). In contrast to synthetic dye-based indicators, FP-based indicators are delivered to the cell as their corresponding DNA coding sequences and can include additional sequences for expression in specific tissues or targeted to specific subcellular compartments.

Early examples of low affinity indicators include DIER and D4cpv, which are based on $Ca^{2+}$-dependent Förster Resonance Energy Transfer (FRET) between cyan and yellow FPs. FRET-based indicators are inherently ratiometric, providing quantitative measurements that are not subject to imaging artefacts due to the movement of organelles or the cell. Indicators engineered from single FPs tend to be intensiometric and often provide larger signal changes. The first single FP-based low affinity $Ca^{2+}$ indicator targeted to the ER was CatchER™. More recently, a number of low affinity GCaMP-type $Ca^{2+}$ indicators have been discovered and are composed of circularly permutated (cp) FP fused to calmodulin (CaM) and a peptide that binds to the $Ca^{2+}$ bound form of CaM. These include the CEPIA™, LAR-GECO™, and ER-GCaMP™ series. Another low affinity single FP-based $Ca^{2+}$ indicator that is emission ratiometric is GEM-CEPIA1er™, but it requires excitation with high-energy ultraviolet light (≤400 nm), which is often associated with increased phototoxicity and autofluorescence.

It may be desirable to use indicators that can be excited with longer wavelengths (i.e., more red-shifted or >400 nm) light as they are often associated with decreased phototoxicity and autofluorescence.

This background information is provided for the purpose of making known information believed by the applicant to be of possible relevance to the present invention. No admission is necessarily intended, nor should be construed, that any of the preceding information constitutes prior art against the present invention.

SUMMARY

In one aspect, the invention may comprise A method of detecting changes in $Ca^{2+}$ levels in a cell, the method comprising:

(a) obtaining a sample comprising cells engineered to express one or more low affinity $Ca^{2+}$ indicator selected from the group consisting of: LAR-GECO1.5, LAR-GECO2, and LAR-GECO3, LAR-GECO4, LAREX-GECO1, LAREX-GECO2, LAREX-GECO3, and LAREX-GECO4, or a polypeptide having a substantially similar amino acid sequence to any one of the foregoing;

(b) exposing the cells to excitation light; and (c) detecting changes in ER, SR and/or mitochondria $Ca^{2+}$ levels by visualizing or imaging the cells.

In another aspect, the invention may comprise a low affinity fluorescent $Ca^{2+}$ polypeptide selected from the group consisting of: LAR-GECO1.5, LAR-GECO2, and LAR-GECO3, LAR-GECO4, LAREX-GECO1, LAREX-GECO2, LAREX-GECO3, and LAREX-GECO4, or a polypeptide having a substantially similar amino acid sequence to any one of the foregoing. In some embodiments, the polypeptide may have the amino acid sequence of one of SEQ ID NOs. 4, 6, 8, 10, 12, 14, 16 or 18.

In some embodiments, the polypeptide may comprise a mutation selected from the group consisting of: I54A, 1330M, and D327N/1330M/D363N. The polypeptide may have a $K_d$ for $Ca^{2+}$ greater than 20 μM, or preferably about 60 μM.

In another aspect, the invention may comprise a polynucleotide encoding a low affinity fluorescent $Ca^{2+}$ polypeptide of the present invention, or a substantially similar polynucleotide sequence. In some embodiments, the polynucleotide may comprise a nucleic acid sequence selected from the group consisting of:

(a) SEQ ID NO. 3, 5, 7, 9, 11, 13, 15, or 17;

(b) a nucleic acid sequence having at least 90% sequence identity to one of SEQ ID NO. 3, 5, 7, 9, 11, 13, 15, or 17, and encoding a fluorescent $Ca^{2+}$ indicator, having a $K_d$ for $Ca^{2+}$ greater than 20 μM, or optionally about 60 μM, but excluding SEQ ID NO. 1;

(c) a nucleic acid sequence encoding a fluorescent $Ca^{2+}$ indicator comprising an amino acid sequence of SEQ ID No. 4, 6, 8, 10, 12, 14, 16 or 18; and (d) a nucleic acid sequence encoding a fluorescent $Ca^{2+}$ greater than 20 μM, or optionally about 60 μM, and having at least 90% sequence identity to an amino acid sequence of SEQ ID No. 4, 6, 8, 10, 12, 14, 16 or 18, but excluding SEQ ID NO. 2.

In some embodiments, the polynucleotide comprises a mutation which encodes an amino acid mutation selected from the group consisting of: 154A, 1330M, and D327N/1330M/D363N.

In other aspects, the invention may comprise a vector or a host cell comprising a polynucleotide sequence of the present invention. In some embodiments, the host cell is a cardiomyocyte.

BRIEF DESCRIPTION OF THE DRAWINGS

Referring to the drawings, several aspects of the present invention are illustrated by way of example, and not by way of limitation, in detail in the figures, wherein.

DETAILED DESCRIPTION

The detailed description set forth below and the appended drawings are intended as a description of various embodiments of the present invention and is not intended to represent the only embodiments contemplated by the inventor. The detailed description includes specific details for the purpose of providing a comprehensive understanding of the present invention, however, the claimed invention may not be limited by such specific details.

Examples of the present invention may provide a toolbox of novel red shifted low affinity $Ca^{2+}$ indicators with a useful dynamic range and $Ca^{2+}$ affinity, as well as polynucleotide sequences encoding such indicators. The $Ca^{2+}$ indicators described herein may be selectively expressed and retained in organelles by fusing organelle-specific targeting sequences to the indicator molecule. Thus, these indicators can be targeted to high concentration $Ca^{2+}$ stores, for example the SR in cultured cardiomyocytes or the mitochondria, and can be imaged alone or in combination with other indicators, enabling direct visualization of an important aspect of disease relevant biology that to date has typically been studied indirectly.

Figure 1:
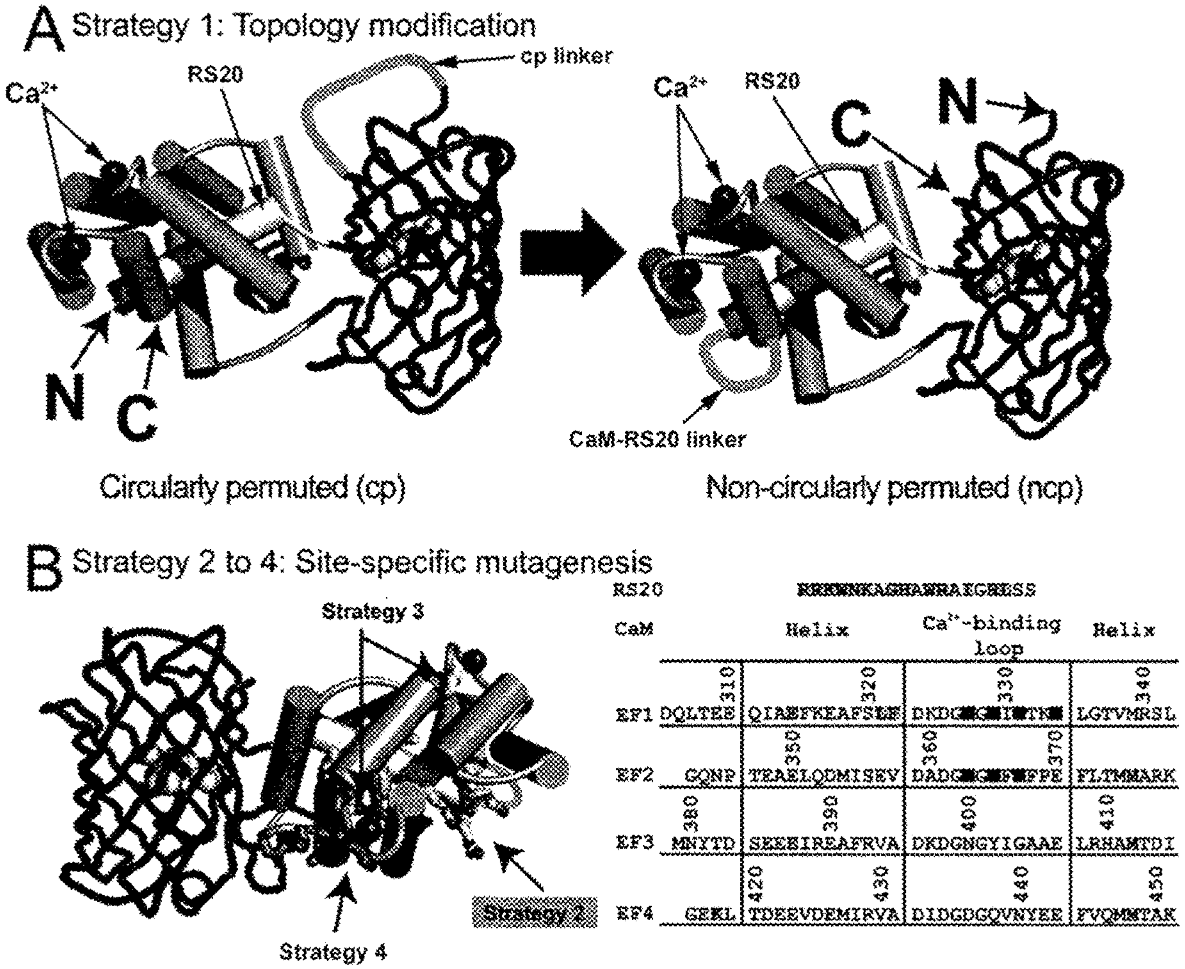
FIG. 1 shows schematic strategies for engineering of low affinity $Ca^{2+}$ indicators.
Figure 2:
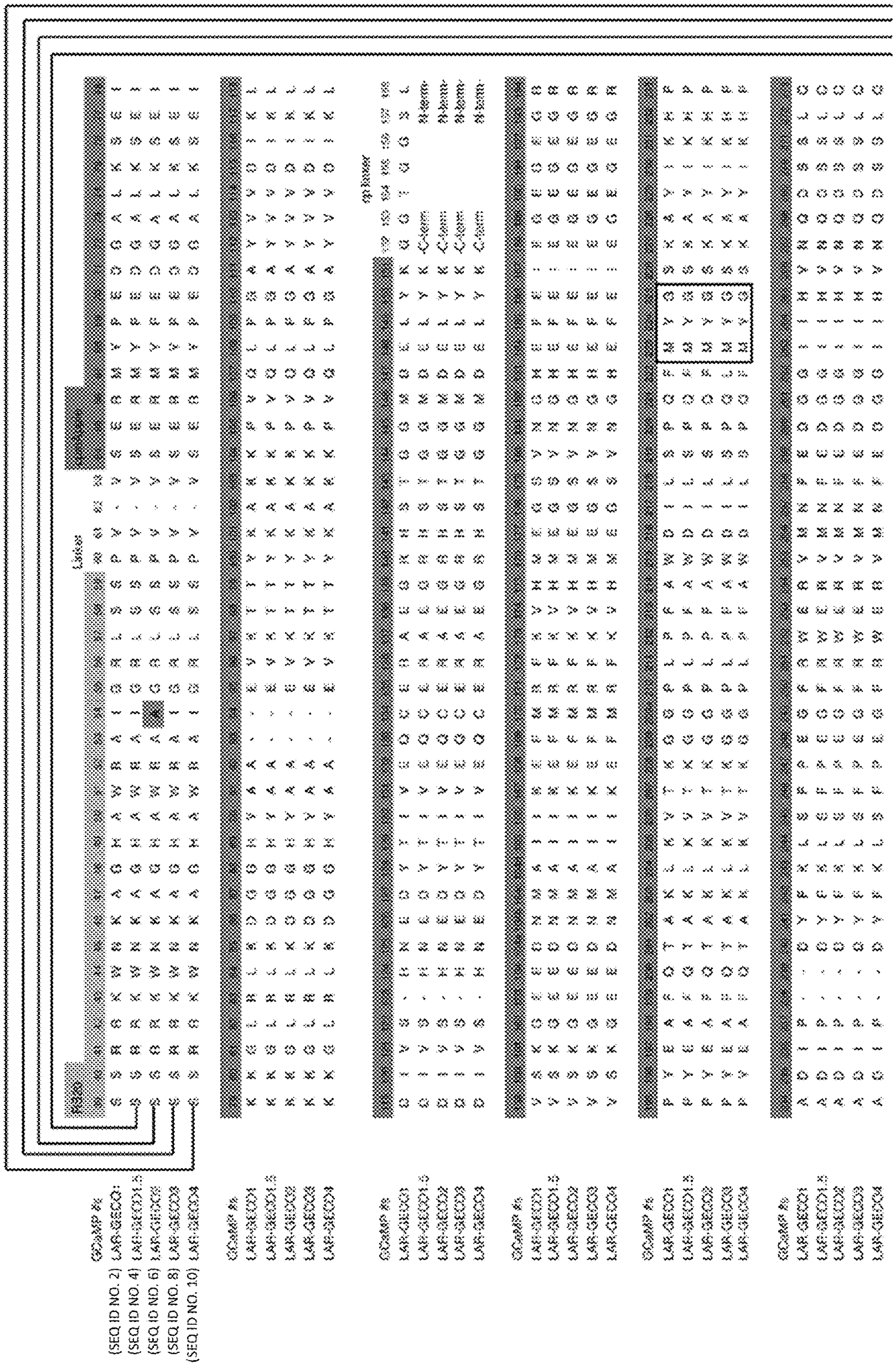
FIG. 2 shows an amino acid sequence alignment for LAR-GECO1 [SEQ ID NO. 2], LAR-GECO1.5 [SEQ ID NO. 4], LAR-GECO2 [SEQ ID NO. 6], LAR-GECO3 [SEQ ID NO. 8], and LAR-GECO4 [SEQ ID NO. 10].
Figure 3:
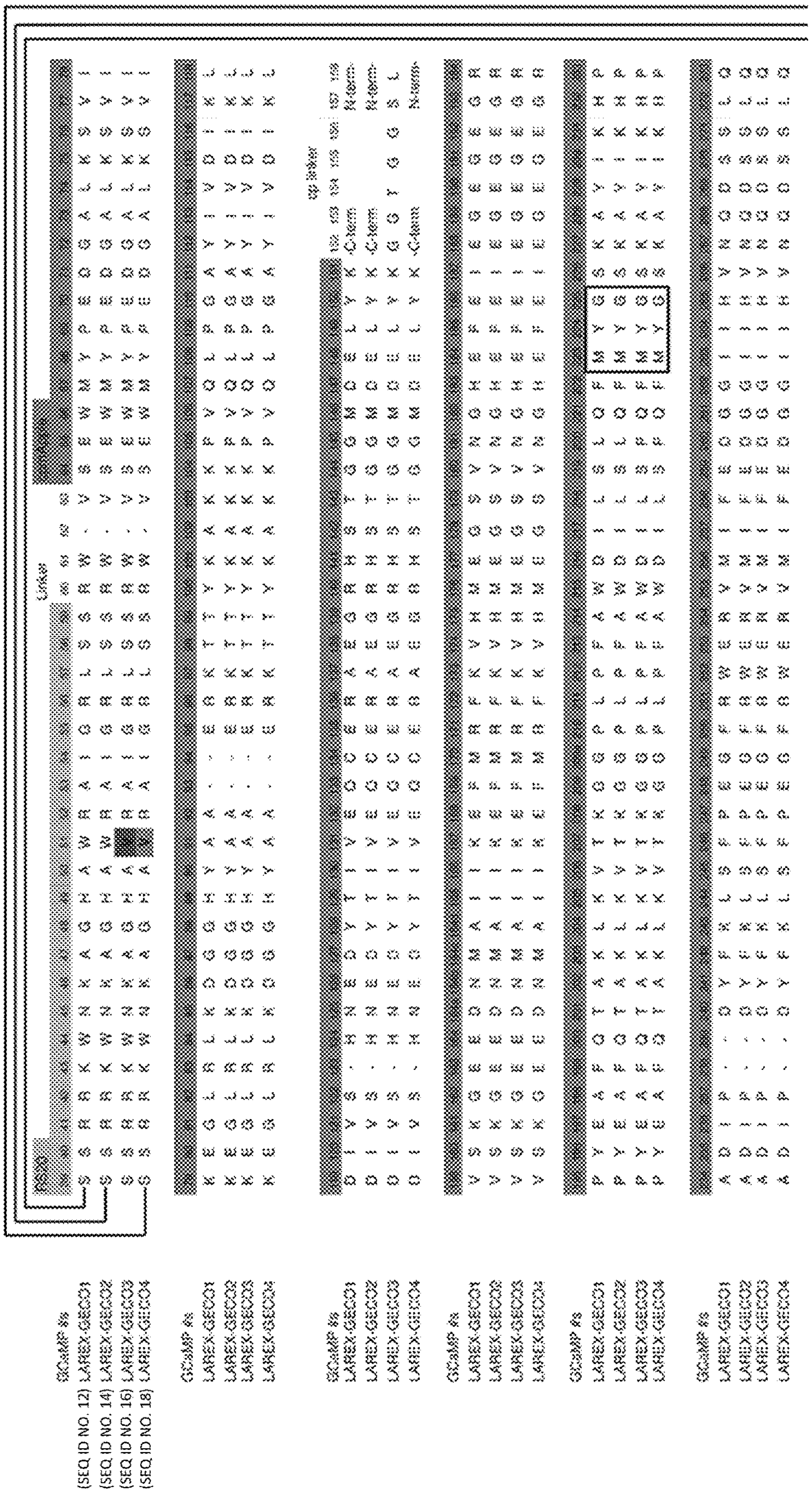
FIG. 3 shows an amino acid sequence alignment of LAREX-GECO1 [SEQ ID NO. 12], LAREX-GECO2 [SEQ ID NO. 14], LAREX-GECO3 [SEQ ID NO. 16], and LAREX-GECO4 [SEQ ID NO. 18].

In some embodiments, the invention may comprise intensiometric red fluorescent low affinity $Ca^{2+}$ indicators derived from LAR-GECO1 ($K_d$=24 μM) [SEQ ID NO. 2]. To engineer intensiometric red fluorescent low affinity $Ca^{2+}$ indicators, the dissociation constant of LAR-GECO1 was tuned by altering the interaction between calmodulin (CaM) and a short peptide from chicken gizzard myosin light chain kinase (RS20) and by modifying CaM's affinity for $Ca^{2+}$. With reference to FIG. 1, different strategies were pursued in the synthesis of the red fluorescent low affinity $Ca^{2+}$ indicators as described herein.

A first strategy involved modification of the indicator topology by fusing the N-terminus of RS20 to the C-terminus of CaM, while reinstating the original non-circularly permutated (ncp) FP termini (i.e. a "camgaroo" topology, so called because the smaller companion is carried the pouch of the indicator). The structure of circularly permuted (cp) R-GECO1 (PDB ID 412Y), which is used here to represent the LAR-GECO1 variant, is shown on the left side of FIG. 1A. The red fluorescent protein domain is linked to the $Ca^{2+}$ binding domain comprised of calmodulin (unlabeled cylinders) and RS20 (labeled cylinder). $Ca^{2+}$ is represented as labeled spheres. On the right side of FIG. 1A is a representation of the non-circularly permuted (ncp) LAR-GECO1.5 [SEQ ID NO. 4]. The cp linker or the CaM-RS20 linker for the ncp topology are labeled.

Alternative strategies involved site-specific mutagenesis, for example, alanine-scanning of the CaM-RS20 interface to weaken this interaction, incorporation of mutations at positions outside of the $Ca^{2+}$ binding sites, or incorporation of mutations in the $Ca^{2+}$-binding sites of CaM. Examples of the second, third and fourth strategies are shown schematically in FIG. 1B. On the left, the LAR-GECO1.5 structure is shown with the targeted residues from strategies 2 to 4 highlighted. On the right, primary sequence of RS20 and CaM with targeted residues highlighted as in LAR-GECO1.5 structure.

Based on strategy 1 shown in FIG. 1, LAR-GECO1 was converted to the ncp topology resulting in LAR-GECO1.5, in which CaM and RS20 are connected by a Gly-Gly-Gly-Gly-Ser-Val-Asp linker, and wherein the FP terminuses are restored. Without restriction to a theory, there may be two possible advantages for this altered topology. The first is that the linker between RS20 and CaM could be engineered to potentially alter the effective $K_d$. The second is that, due to the direct linkage between RS20 and CaM, they could be less available for interaction with endogenous proteins in the ER or SR.

Figure 4:
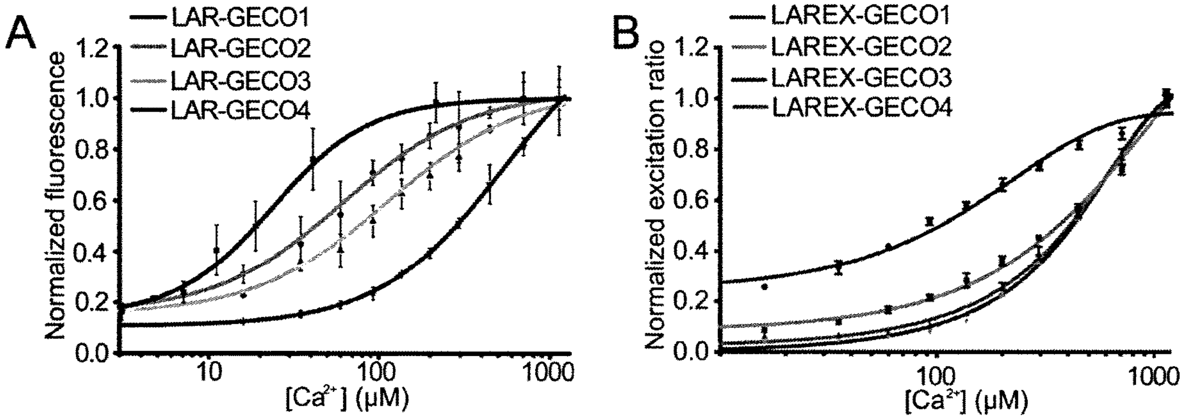
FIG. 4 shows intensiometric and ratiometric red $Ca^{2+}$ indicators with a wide range of affinities to $Ca^{2+}$.

LAR-GECO1.5 has a similar $Ca^{2+}$ affinity as LAR-GECO1, while maintaining a fluorescent response to $Ca^{2+}$ of 7.4-fold, indicating that ncp topology does not adversely affect this function. FIG. 4 shows normalized fluorescence intensity as a function of free $Ca^{2+}$ concentration in buffer (10 mM MOPS, 100 mM KCl, pH 7.2). LAR-GECO1.5's trace is essentially identical to LAR-GECO1. Consequently, the ncp topology was retained for the design and engineering of low affinity $Ca^{2+}$ indicators.

Using the LAR-GECO1.5 as a template, strategies 2, 3, and 4 (and/or combinations thereof) were explored to create genetic variants and express them in the context of *Escherichia coli* colonies. Fluorescence imaging of colonies was used to identify brightly fluorescent clones, which were picked, cultured, and tested for their $Ca^{2+}$ response and affinity. This procedure led to the identification of three exemplary indicators with a decreased affinity to $Ca^{2+}$.

Among the alanine-scanning constructs, an indicator (designated LAR-GECO2 [SEQ ID NO. 6]) with the Ile54Ala mutation exhibits a $Ca^{2+}$ $K_d$ of 60 μM and a 5.7-fold increase in fluorescence upon binding to $Ca^{2+}$ was discovered. Based on an Ile330Met mutation, an indicator (designated LAR-GECO3 [SEQ ID NO. 8]) with a $K_d$ of 110 μM and a fluorescent response to $Ca^{2+}$ of 7.5-fold was discovered. Based on mutations of Asp327Asn, Ile330Met, and Asp363 Asn, an indicator (designated LAR-GECO4 [SEQ ID NO. 10]) with a $K_d$ of 540 UM and a fluorescent response to $Ca^{2+}$ of 13-fold was discovered.

The low affinities of LAR-GECO2, 3 and 4 are related to the identified mutations, therefore, some embodiments of the invention may include variant polypeptides which vary in other domains, but retain the same or similar functionality and retain one or more of these mutations.

Figure 7:
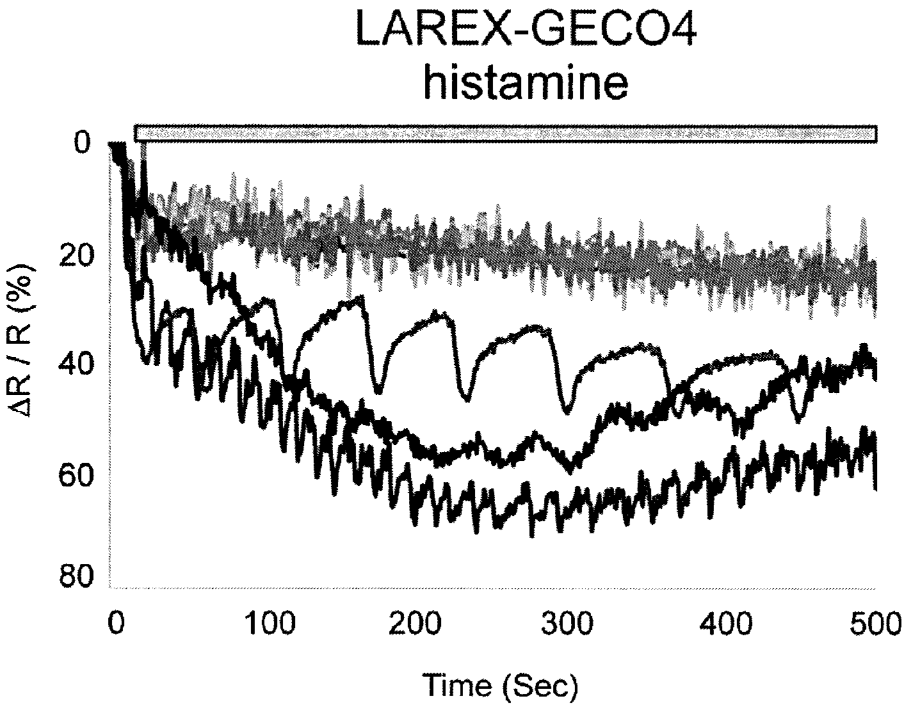
FIG. 7 shows that ER-LAREX-GECO4 (n=7) expressed in Hela Cells can detect SR $Ca^{2+}$ dynamics following histamine stimulations. ΔR/R=(Rinit−R)/Rinit*100%, where R is the ratio of emission intensity with excitation at 470 nm to emission intensity with excitation at 595 nm, Rinit is the initial ratio. 20 μM histamine application is indicated by the gray bar.

Genetic fusing of all the indicators to ER targeting and retention sequences and expression in HeLa cells exhibited the expected pattern of ER-localization and bright red fluorescence. FIG. 7 shows that ER-LAREX-GECO4 expressed in HeLa cells can detect ER/SR $Ca^{2+}$ dynamics following histamine stimulations.

TABLE 1

In vitro characterisation of the LAR-GECO series

| Protein | $Ca^{2+}$ | λabs (nm) (ε) ($mM^{-1} \cdot cm^{-1}$) | λem (nm) (φ) | Brightness[1] ($mM^{-1} \cdot cm^{-1}$) | $pK_a$ | Intensity change ± $Ca^{2+}$ | $K_d$ for $Ca^{2+}$ (μM), (Hill coefficient) |
|---|---|---|---|---|---|---|---|
| LAR- | − | 574 (5.3) | 598 (0.13) | 0.69 | 8.6 | 10x | 24 (1.3) |
| GECO1 | + | 561 (35.8) | 589 (0.20) | 7.2 | 5.4/8.8[2] | | |
| LAR- | − | 574 (9) | 599 (0.19) | 1.7 | 9.3 | 7.4x | 24 (1.1) |
| GECO1.5 | + | 561 (47) | 587 (0.27) | 12 | 6.0/9.0[2] | | |
| LAR- | − | 574 (5.0) | 598 (0.13) | 0.65 | 8.9 | 5.7x | 60 (1.2) |
| GECO2 | + | 561 (19.7) | 589 (0.19) | 3.7 | 6.4/9.0[2] | | |
| LAR- | − | 574 (5.5) | 598 (0.11) | 0.61 | 9.4 | 7.5x | 110 (1.1) |
| GECO3 | + | 561 (23.2) | 589 (0.20) | 4.6 | 5.9/8.8[2] | | |
| LAR- | − | 574 (5.3) | 598 (0.10) | 0.53 | 9.1 | 13x | 540 (1.2) |
| GECO4 | + | 561 (35.2) | 589 (0.19) | 6.7 | 6.5/8.8[2] | | |

[1]Brightness is defined as the product of ε and φ.
[2]In the $Ca^{2+}$-bound state, all LAR-GECOs show biphasic pH dependence.

Thus, as summarised in Table 1, LAR-GECO2, −3 and −4 are red fluorescent $Ca^{2+}$ indicators that are intensiometric and have lower affinities than their parental indicator LAR-GECO1.

In another aspect, the invention comprises ratiometric low affinity red GECOs. In some embodiments, these indicators have ratiometric properties, which can reduce sensitivity to movement, improve quantitative measurement and enable single wavelength excitation with two-colour imaging strategies. Thus, in some embodiments, the present invention comprises at least four new ratiometric low affinity red GECOs with affinities to $Ca^{2+}$ ranging from 146 μM to 1023 μM, described here as LAREX-GECOs.

These novel new indicators were derived from REX-GECO1, a previously reported excitation ratiometric red $Ca^{2+}$ indicator, which was engineered into the ncp topology. Then the same mutations used to engineer LAR-GECO3 and −4 above were then introduced, to produce new indicators LAREX-GECO1 [SEQ ID NO. 12] and LAREX-GECO2 [SEQ ID NO. 14]. FIG. 4, panel B, shows normalized excitation ratio as a function of free $Ca^{2+}$ concentration in buffer (10 mM MOPS, 100 mM KCl, pH 7.2). Excitation ratio=480 nm/580 nm excitation fluorescence intensity ratio. $K_d$ is dissociation constant of $Ca^{2+}$. Relative to REX-GECO1 ($K_d$ of 240 nM), the novel indicators, designated as LAREX-GECO1 and LAREX-GECO2, provide substantially lower $Ca^{2+}$ affinities of 146 μM and 1023 μM, respectively.

In other embodiments, further LAREX-GECOs derivatives were produced, wherein the CaM portion of REX-GECO1 was replaced with the CaM portion of R-CEPIAler, a previously reported intensiometric low affinity red $Ca^{2+}$ indicator. The resulting new indicator, designated as LAREX-GECO3 [SEQ ID NO. 16], exhibits a $Ca^{2+}$ $K_d$ of 564 μM and a dynamic range of 23-fold. Converting LAREX-GECO3 protein to the ncp topology resulted in another new indicator, designated as LAREX-GECO4 [SEQ ID NO. 18] with a similar $K_d$ of 593 μM and a dynamic range of 18-fold.

The characterisation of LAREX-GECOs is summarised in table 2.

TABLE 2

Summary of Ratiometric Indicators

| Protein | $Ca^{2+}$ | λabs (nm) (ε) ($mM^{-1}$ $cm^{-1}$) | λem (φ) | Brightness[1] ($mM^{-1} \cdot cm^{-1}$) | pKa[3] | Ratio change[2] ± $Ca^{2+}$ | $K_d$ for $Ca^{2+}$ (μM), (Hill coefficient) |
|---|---|---|---|---|---|---|---|
| LAREX-GECO1 | − | 578 (39) | 605 (0.14) | 5.5 | 6.1 | 4.5x | 146 (0.93) |
| | + | 467 (29) | 586 (0.14) | 4.0 | | | |
| LAREX-GECO2 | − | 578 (36) | 605 (0.13) | 4.7 | 5.7 | 23x | 1023 (0.8) |
| | + | 471 (32) | 586 (0.20) | 6.4 | | | |
| LAREX-GECO3 | − | 579 (39) | 605 (0.08) | 3.1 | 6.5 | 23x | 564 (1.7) |
| | + | 474 (32) | 587 (0.17) | 5.4 | | | |

TABLE 2-continued

Summary of Ratiometric Indicators

| Protein | $Ca^{2+}$ | λabs (nm) (ε) ($mM^{-1}$ $cm^{-1}$) | λem (φ) | Brightness[1] ($mM^{-1}$ · $cm^{-1}$) | pKa[3] | Ratio change[2] ± $Ca^{2+}$ | $K_d$ for $Ca^{2+}$ (μM), (Hill coefficient) |
|---|---|---|---|---|---|---|---|
| LAREX-GECO4 | − | 578 (33) | 605 (0.08) | 2.6 | 6.2 | 18x | 593 (1.6) |
| | + | 471 (31) | 587 (0.17) | 5.3 | | | |

[1]Brightness is defined as the product of ε and φ.
[2]Defined as the change of the excitation ratio (450 nm/580 nm).
[3]$pK_a$ is the pH at which the dynamic range is 50% of maximum.

Table 3 provides a summary of the calcium affinity of the indicators. Characterization of these indicators is described below.

TABLE 3

Summary of $Ca^{2+}$ indicators

| Name | $K_d$ (μM) | Topology |
|---|---|---|
| LAR-GECO1 | 24 | cp |
| LAR-GECO1.5 | 24 | ncp |
| LAR-GECO2 | 60 | ncp |
| LAR-GECO3 | 110 | ncp |
| LAR-GECO4 | 540 | ncp |
| LAREX-GECO1 | 146 | ncp |
| LAREX-GECO2 | 1023 | ncp |
| LAREX-GECO3 | 564 | cp |
| LAREX-GECO4 | 593 | ncp |

Observing $Ca^{2+}$ Dynamics in Heart Muscle Cells

In heart muscle cells, called cardiomyocytes, contraction and relaxation requires cyclical release and reuptake of $Ca^{2+}$, which consequently is a critical regulator of contraction. Typically, cytoplasmic concentrations change from a diastolic range (~0.1 μM free $Ca^{2+}$) to a systolic range one order of magnitude higher (~1 μM free $Ca^{2+}$). As intracellular $Ca^{2+}$ buffering is significant, ~100 μM total $Ca^{2+}$ is required to effect this change. Most of the required $Ca^{2+}$ comes from the SR, which comprises only a fraction of the cell volume, and therefore contains $Ca^{2+}$ concentrations much higher than the cytoplasm. As a result, observation of $Ca^{2+}$ dynamics in the SR is difficult due to lack of low affinity $Ca^{2+}$ indicators. For this reason, indirect measurements of cytoplasmic $Ca^{2+}$ in response to caffeine induced SR emptying in the presence or absence of various chemical inhibitors is typically used.

The low affinity $Ca^{2+}$ dye Fluo-5N ($K_d$=97 μM) has been used to visualize SR $Ca^{2+}$ changes in isolated permeabilized adult ventricular myocytes but specific SR loading without cytoplasmic contamination may be difficult to achieve and as an intensiometric indicator, it may be susceptible to motion artefact. Stem cell derived cardiomyocytes lack the typical spatial T-tubule/SR architecture seen in ventricular myocytes and erroneous cytoplasmic signals therefore cannot be identified based on positional information.

In one embodiment, the indicators of the present invention may mitigate these challenges and provide physiological beat-to-beat changes in SR $Ca^{2+}$, which can be directly visualised in a cell culture; and stem cell derived cardiomyocytes.

Physiological Changes in SR $Ca^{2+}$ Visualised in a Cell Culture

A large variety of models are used in cardiovascular research. In one aspect of the present invention a cell culture of stable immortalized cell lines, known as the HL1 cell line, derived from mouse atrial cardiomyocytes is used as a model.

Figure 8:
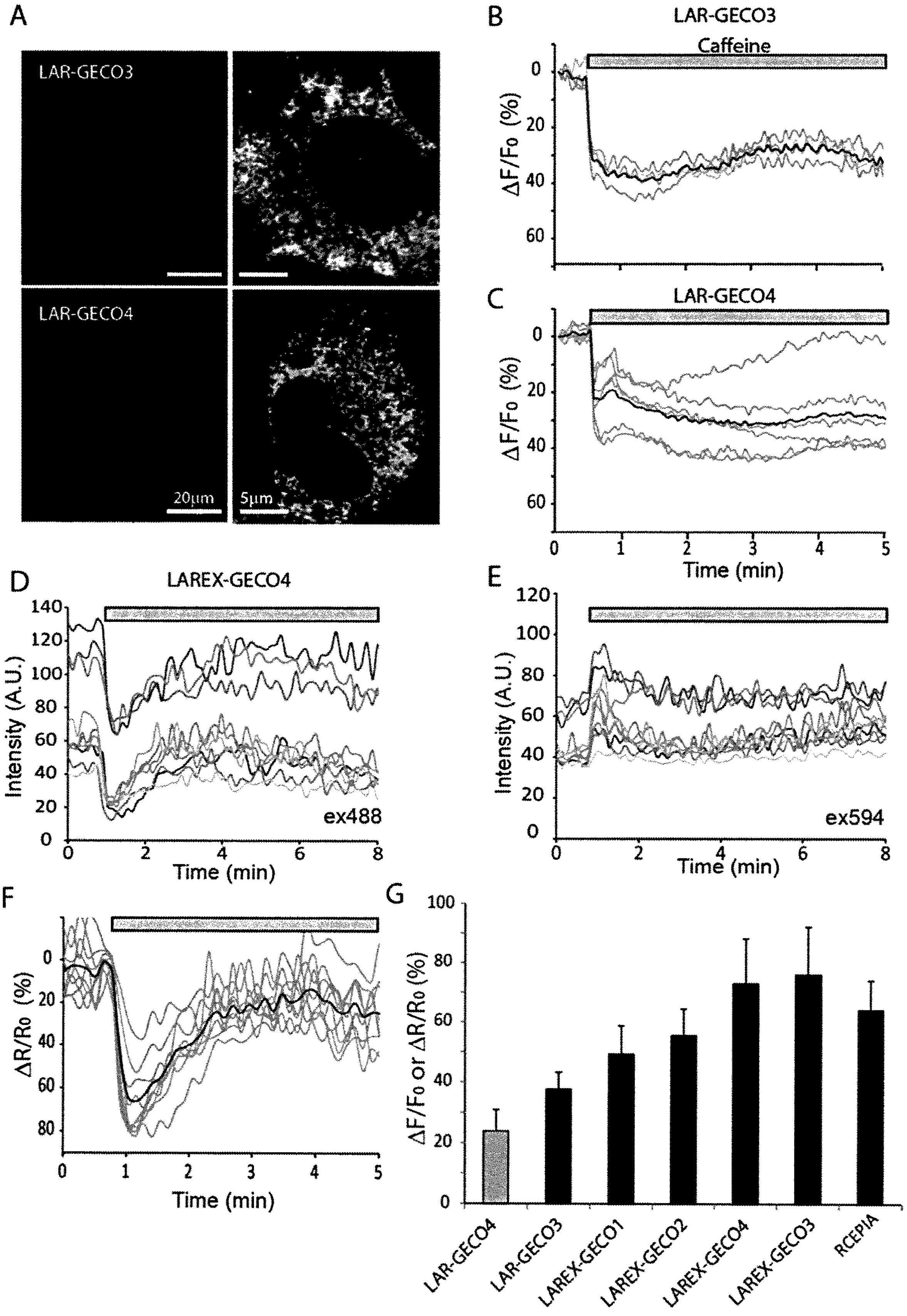
FIG. 8 shows a comparison of low affinity $Ca^{2+}$ indicators in the immortalized mouse atrial HL1 cell line. (A) Expression of ER-LAR-GECO3 and ER-LAR-GECO4 in HL1 cells. Live cell images are on the left, fixed images of ER-LAR-GECO3 and ER-LAR-GECO4 taken by confocal microscopy are shown on the right in greyscale. Observation of ER/SR $Ca^{2+}$ change in response to caffeine stimulation with ER-LAR-GECO3 (B), ER-LAR-GECO4 (C) and ER-LAREX-GECO4 (D-F). Ratiometric stimulation of ER-LAREX-GECO4 was achieved with laser illumination at 488 nm (D) and 594 nm (E). (F) $\Delta R/R_0$ trace was calculated from (D) and (E). (G) Comparison of performance for ER-LAR-GECO4 (n=21), ER-LAR-GECO3 (n=14), ER-LAREX-GECO2 (n=8), ER-LAREX-GECO1 (n=7), ER-LAREX-GECO4 (n=14), ER-LAREX-GECO3 (n=8), R-CEPIAer (n=15). For intensiometric indicators, $\Delta F_{SR}=(F_{init}-F_{caf})/F_{init}*100\%$, where F is the fluorescence intensity, $F_{init}$ is the initial intensity, and $F_{caf}$ is the intensity immediately following caffeine addition. For ratiometric indicators, $\Delta R_{SR}=(R_{init}-R_{caf})/R_{init}*100\%$, where R is the ratio of emission intensity with excitation at 488 nm to emission intensity with excitation at 594 nm, $R_{init}$ is the initial ratio and $R_{caf}$ is the ratio immediately following caffeine addition.
Figure 11:
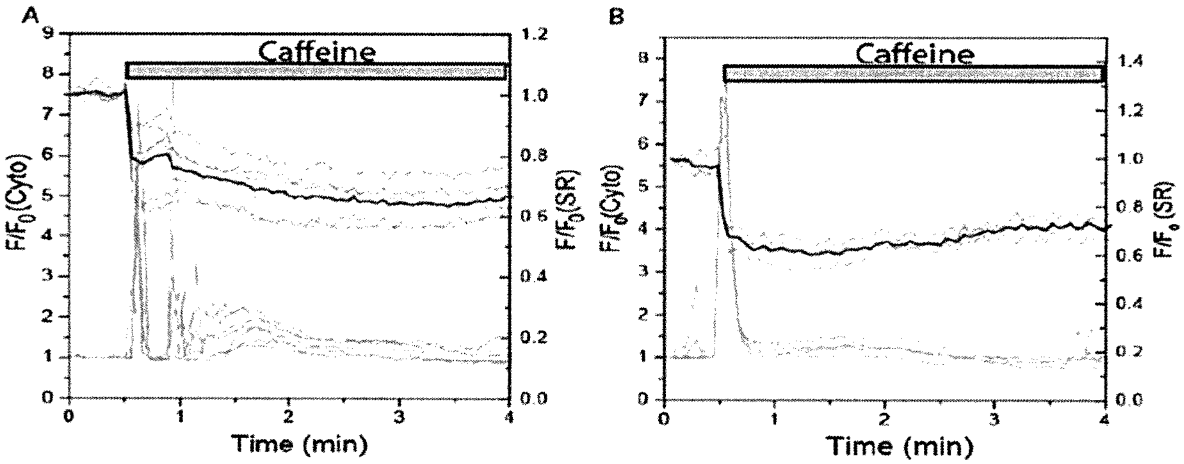
FIG. 11 shows observation of cytosolic $Ca^{2+}$ and ER/SR $Ca^{2+}$ change in response to caffeine stimulation by G-GECO1 with (A) ER-LAR-GECO4 and (B) ER-LAR-GECO3 in HL1 cells. The thick grey trace represents the averaged response of the G-GECO1 cytoplasmic emission with the associated left y axis scale bar (F/Fo (Cyto)). The thick black trace represents the averaged response of the SR targeted red shifted indicator, with the right y axis scale bar ((F/Fo (SR)). Individual cell responses are shown in thin grey traces. Caffeine application is indicated by the grey bar.

With reference to FIG. 8 (panels A, B and C) and FIG. 11, ER-LAR-GECO3 and ER-LAR-GECO4 were evaluated with the simultaneous expression of cytoplasmic G-GECO1 in the HL1 cell line. In response to 10 mM caffeine addition, a rise in the cytosolic $Ca^{2+}$ signal can be accompanied by a decrease in the ER/SR $Ca^{2+}$ signal.

With reference to FIG. 8, panels D, E and F, ratiometric imaging of ER-LAREX-GECO4 was achieved by dividing the emission intensity with excitation at 488 nm with the emission intensity at 594 nm excitation.

With reference to FIG. 8, panel G, a comparison of the intensiometric or ratiometric responses of the various indicators of the present invention upon caffeine stimulation ($\Delta F_{SR}$ or $\Delta R_{SR}$) in the HL1 cell line show that ER-LAREX-GECO4 and ER-LAREX-GECO3 have the largest signal changes (−72.9+/−15.2% and −76.0+/−16.1% change, respectively). The present invention also provides in vitro characterization demonstrating ER-LAREX-GECO4 (dynamic range 18×, $K_d$=593 μM) and ER-LAREX-GECO3 (dynamic range 23×, $K_d$=564 μM) having large dynamic ranges and optimal $K_d$ values for detection of cyclical diastolic (~1000 to 1500 μM) to systolic (~300 to 600 μM) $Ca^{2+}$ changes in the cardiomyocyte of the SR.

Physiological Changes in SR $Ca^{2+}$ Visualised in Stem Cells

In another aspect, the indicators described herein may provide visualization of changes in SR $Ca^{2+}$ levels, such as in cardiomyocytes derived from human embryonic stem cells (hES) or human induced pluripotent stem cells (hiPSCs). Such stem cells can be a model of inherited heart disease or in vitro drug toxicity and drug screening platforms.

Figure 9:
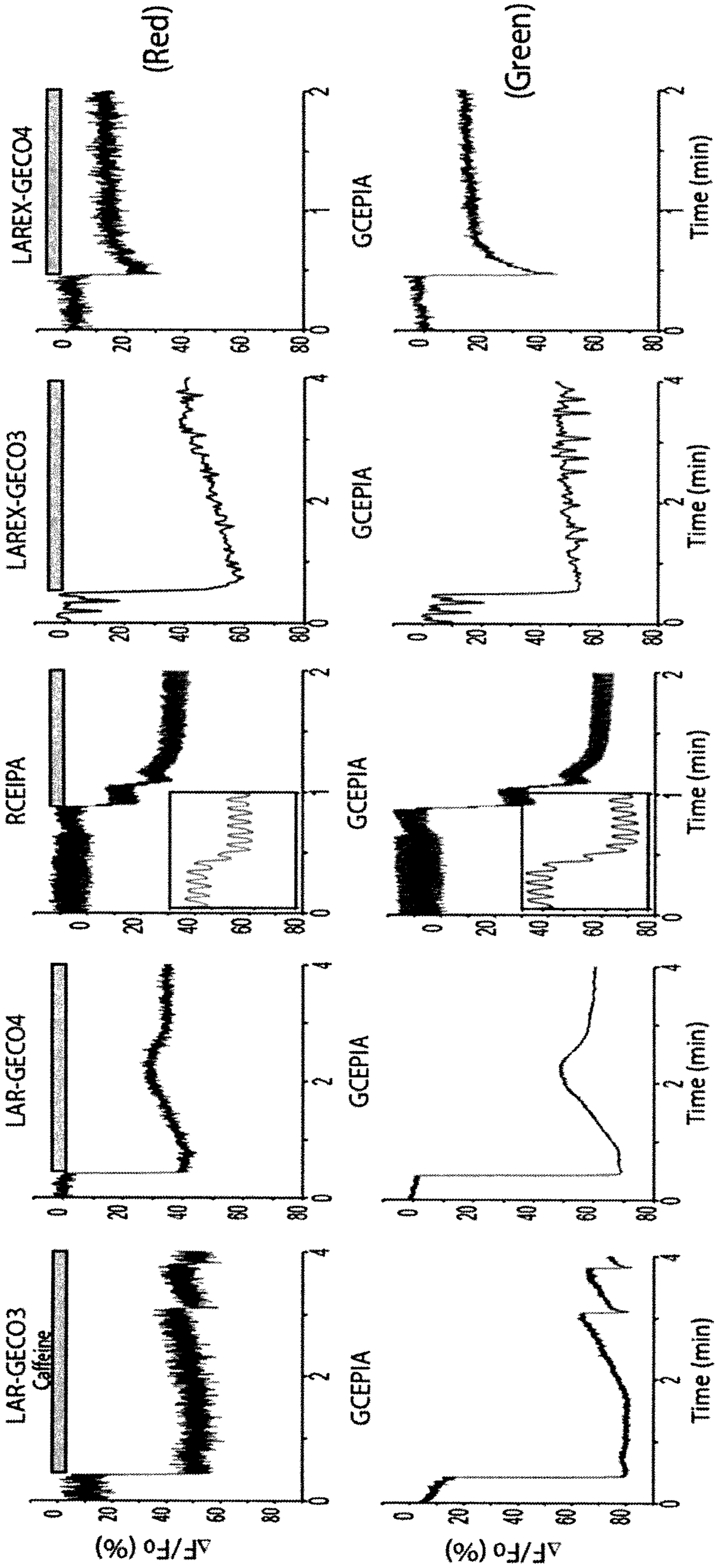
FIG. 9 shows a comparative performance of ER-LAR-GECOs and ER-LAREX-GECOs in human embryonic stem cell derived cardiomyocytes (hES-CMs) relative to a G-CEPIAer benchmark. hES-CMs were co-transfected with ER-LAR-GECOs, ER-LAREX-GECOs or R-CEPIAer, together with G-CEPIAer. Representative emission signals (vertical pairs of panels) from each reporter pair, in single cells, were obtained simultaneously through a Dual View system. Some cells (i.e., the R-CEPIA-G-CEPIA pair), underwent spontaneous oscillations that coincided with contraction and relaxation. Inset displays time-lapse of hES-CMs expressing G-CEPIAer and R-CEPIAer from 0.8 to 1 min. Caffeine addition is shown by the grey bar.

With reference to FIG. 9, a green low affinity indicator G-CEPIAer (reporting a dynamic range 4.7×, $K_d$=672 μM) was used as an internal standard to minimize the impact of cell phenotype variability and immaturity. The indicators described herein were compared to green low affinity indicator G-CEPIAer, in stem-cell derived cardiomyocytes. The present invention may permit visualization of physiological beat to beat SR emptying in addition to provoked SR $Ca^{2+}$ depletion in response to caffeine application.

From the intensity traces, the response ($\Delta F_{SR}$) of the red indicators, which could be divided by the paired $\Delta F_{SR}$ for G-CEPIAer producing a comparative $R_{red/green}$ ratio in the same cell, ($\Delta F_{SR}$ from red channel/$\Delta F_{SR}$ from G-CEPIAer). ER-LAREX-GECO3 ($R_{red/green}$=1.03+/−0.08) it appears equivalent to the G-CEPIAer. Both ER-LAREX-GECO3 and ER-LAREX-GECO4 ($R_{red/green}$=0.71+/−0.02) appear to perform better than R-CEPIAer ($R_{red/green}$=0.60+/−0.06) in this system, which is consistent with results obtained in HL1 cultured cell line and the in vitro data. Isolated comparisons between cells, for example using the G-CEPIAer traces alone, can reveal significant heterogeneity in individual responses, which could be a weakness of current in vitro stem cell derived cardiomyocyte models.

Ratiometric LAREX-GECO3 and LAREX-GECO4 indicators may offer advantages in the in vitro systems can be further characterized in stem cell models.

Figure 12:
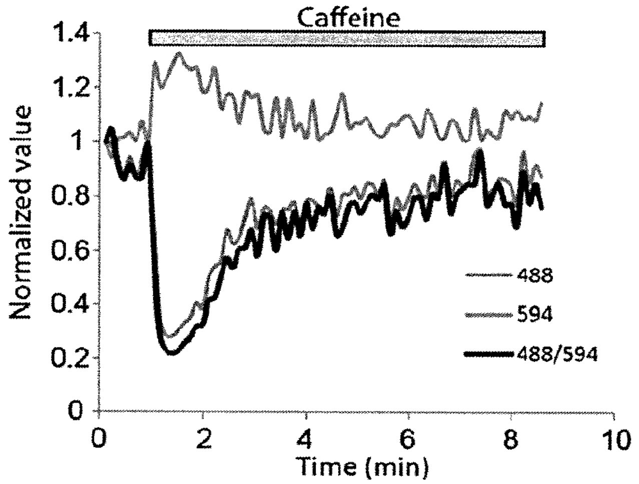
FIG. 12 shows characterization of ER/SR store in human embryonic stem cell derived cardiomyocytes (hES-CM) by ratiometric measurement using ER-LAREX-GECO3. ER-LAREX-GECO3 was excited by with laser illumination at 488 nm and 594 nm. Caffeine depletes the SR store and $Ca^{2+}$ refills slowly with small $Ca^{2+}$ oscillations that are more clearly observed in the ratiometric (black, iii) trace.

An advantage of ratiometric, relative to some intensiometric indicators, is that they self-correct for cell movement. This is a particular problem for caffeine stimulation methods, as emptying of the SR can provoke larger movements than the regular oscillatory contraction and relaxation of the cultured cardiomyocyte. This ratiometric imaging provides observation of spontaneous beat-to-beat $Ca^{2+}$ release and reuptake. With reference to FIG. 12, following a caffeine application to deplete the SR $Ca^{2+}$ concentrations, oscillations during $Ca^{2+}$ reuptake to SR can be easily detected.

Figure 14:
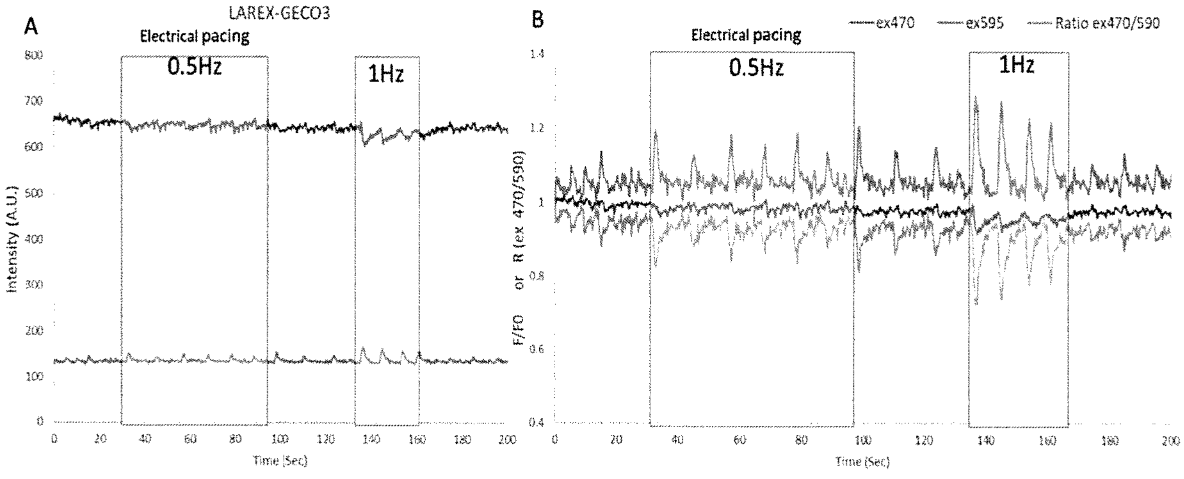
FIG. 14 shows that the ER/SR $Ca^{2+}$ dynamics in iPSC-CMs can be monitored by ratiometric measurement using ER-LAREX-GECO3 under electrical pacing. (A) Time-lapse of iPSC-CMs expressing ER-LAREX-GECO3 in response to electrical pacing at 0.5 Hz and 1.0 Hz. ER-LAREX-GECO3 was excited by LED illumination at 470 nm (i) and 595 nm (ii) for acquiring ratiometric imaging. Signal is observed at 25 Hz. (B) F/FO was calculated from (A), where F is the florescence intensity, FO is the resting intensity. R is ratio of F/FO (ex 470)/F/FO (ex 595) shown in black line (iii). Cells were paced by C-Pace EP (ION OPTIX), voltage condition was set at 15V. The grey boxes indicate the time slot that cells were stimulated with the electrode.
Figure 15:
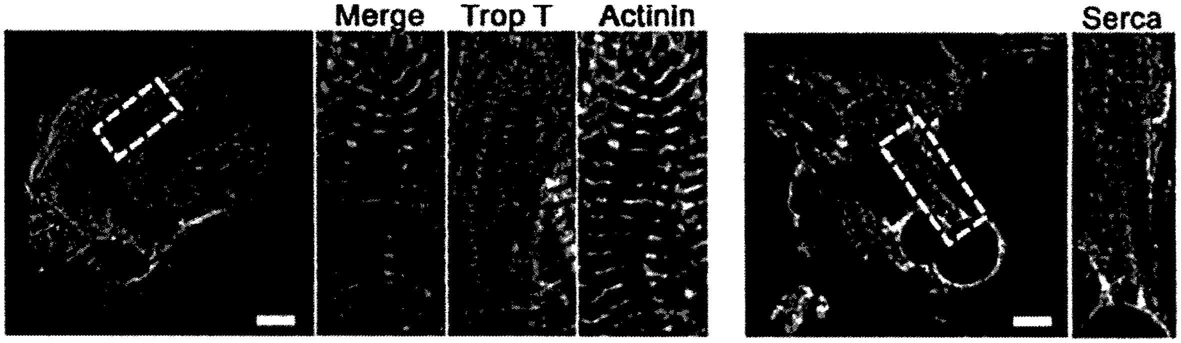
FIG. 15 shows immunofluorescence characterization of stem cell derived cardiomyocytes showing the typical rudimentary circular rather than elongated appearance with immunofluorescence staining of sarcomeric components Troponin-T, and alpha-actinin to confirm cardiomyocyte identity. Within these mixed populations, a small proportion of cells are binucleate with some areas of apparently more organized SERCA staining potentially indicative of an evolving cellular maturity in contrast to FIG. 13A. Scale bar, 10 micron. Zoomed panels taken from the main image as indicated.

In another aspect, changes in beat-to-beat $Ca^{2+}$ concentrations in iPSC-CMs under electrical pacing can also be detected by ER-LAREX-GECO3, as shown in FIG. 14.

Figure 6:
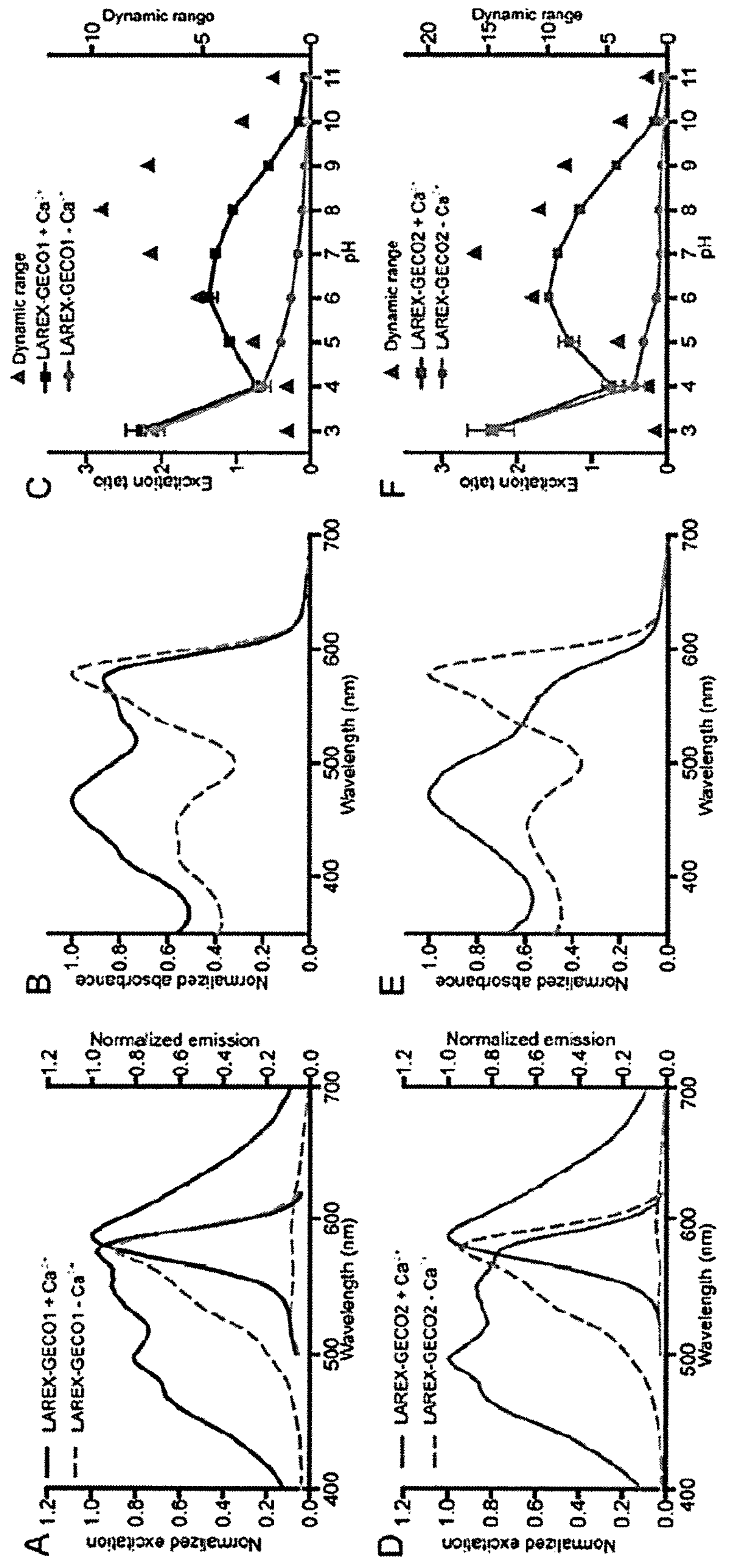
FIG. 6 shows in vitro characterizations of LAREX-GECOs. (A, D, G, and J) Excitation and emission spectra of LAREX-GECO1 (A), LAREX-GECO2 (D), LAREX-GECO3 (G) and LAREX-GECO4 (J). (B, E, H, and K) Absorbance and emission spectra of LAREX-GECO1 (B) and LAREX-GECO2 (E), LAREX-GECO3 (H), and LAREX-GECO4 (K) in both the $Ca^{2+}$-free state (dotted line) and the $Ca^{2+}$-bound state (solid line). (C, F, I, and L) Fluorescence intensity of LAREX-GECO1 (C), LAREX-GECO2 (F), LAREX-GECO3 (I), and LAREX-GECO4 (L) as a function of pH.
Figure 6:
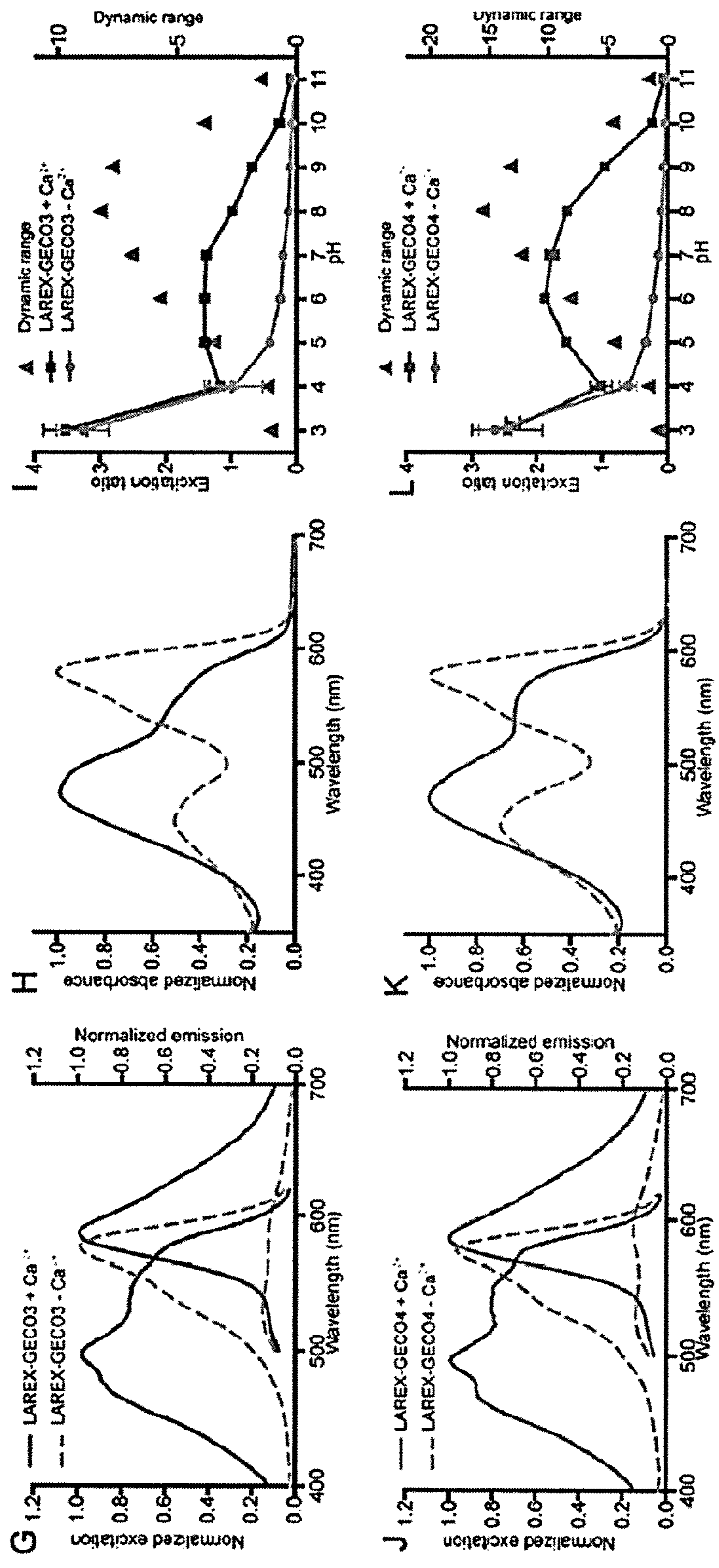
Figure 13:
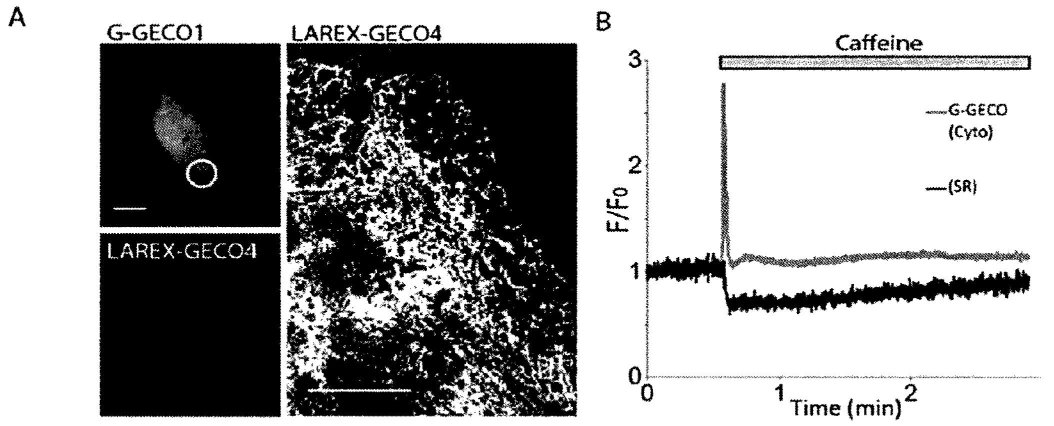
FIG. 13 shows demonstration of single wavelength excitation for observing cytoplasmic $Ca^{2+}$ (G-GECO) and ER/SR $Ca^{2+}$ (ER-LAREX-GECO4) in hES-CM. (A) Excitation of G-GECO and ER-LAREX-GECO4 by blue light is shown. Image of ER-LAREX-GECO4 was further taken by confocal microscopy (right greyscale image) showing the typically unorganised arrangement of the SR in these cell types. (B) Time-lapse of hES-CM responding to caffeine treatment. A 480 nm LED was used to excite both G-GECO and ER-LAREX-GECO4. Signal is simultaneously observed by a dual view system at 10 Hz. Caffeine application is demonstrated by the grey bar.

Since ratiometric indicators have a $Ca^{2+}$ dependent excitation in the blue-green light spectrum, as shown in FIG. 6, which appears to capture most of the information of SR emptying and refilling as shown in FIG. 12, embodiments of the present invention may include single wavelength two-colour imaging using G-GECO1 and ER-LAREX-GECO4 in stem-cell derived cardiomyocytes, as shown in FIG. 13. This avoids the need to switch illumination sources and is therefore a strategy for high frame rate imaging or prolonged observation that can be desirable in some circumstances.

Figure 10:
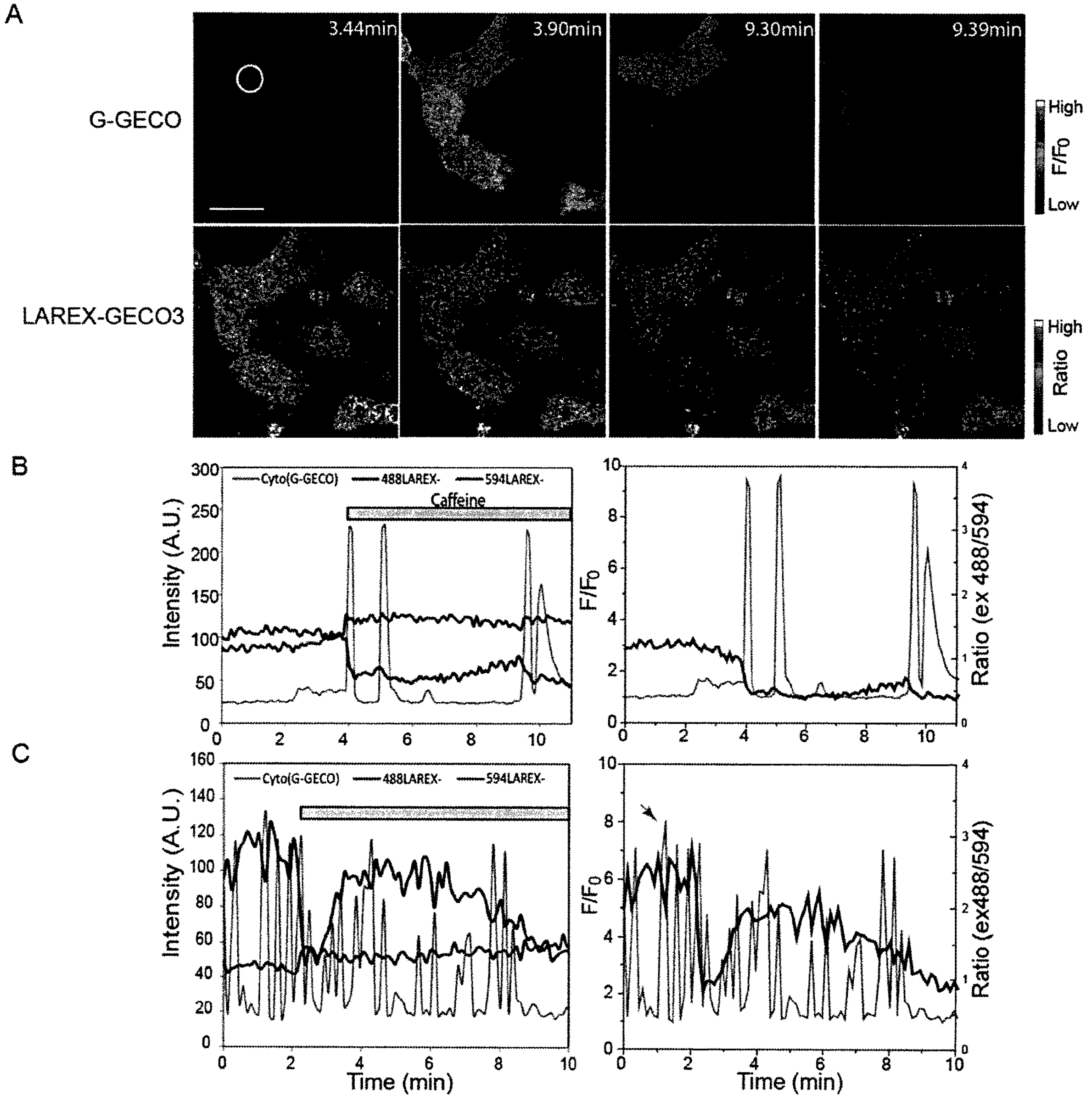
FIG. 10 shows observing cytosolic and SR $Ca^{2+}$ in iPSC derived cardiomyocytes (iPSC-CM). Cells were co-transfected with G-GECO and ER-LAREX-GECO3 to visualize their spontaneous activity and response to caffeine stimulation (grey bar). G-GECO was illuminated by a laser at 488 nm. ER-LAREX-GECO3 was excited by laser illumination at 488 nm and 594 nm. Two types of responses were observed. (A and B) In one group of cells a large initial response to caffeine application was observed, but coupling of spontaneous SR depletion and subsequent $Ca^{2+}$ oscillations were not apparent. (C) A second group of cells demonstrate coupling of spontaneous SR emptying with changes in cytoplasmic $Ca^{2+}$ detectable in iPS-CMs prior to (blue arrow), and following, caffeine application. Intensities in individual emission channels is shown on the left and the processed ratiometric data set is shown on the right.

With reference to FIG. 9, since physiological SR $Ca^{2+}$ depletion may not be detected in all cells expressing G-CEPIA, even though they were all visibly contracting, the present invention may permit the ratiometric measurement of SR $Ca^{2+}$ release with cytosolic $Ca^{2+}$ observation using the co-expression of G-GECO and ER-LAREX-GECO3 in iPSC cardiomyocytes, as shown in FIG. 10.

With reference to FIG. 10 panel B, although some cells appear to have initial coupling between the initial caffeine provoked SR $Ca^{2+}$ depletion and cytoplasmic $Ca^{2+}$ accumulation, it may be seen that subsequent oscillations are not linked. However with reference to FIG. 10 panel C, other cells from the same stem cell differentiation have shown coupling of spontaneous cytosolic $Ca^{2+}$ transients with $Ca^{2+}$ fluctuation in the adjacent SR, indicative of physiological $Ca^{2+}$ release from the SR store contributing to cytosolic $Ca^{2+}$ before caffeine treatment. Following caffeine application these cells show a correlation between the amplitude of cytoplasmic $Ca^{2+}$ transient recovery and the gradual restoration of SR $Ca^{2+}$ content and durable coupling of cytoplasmic and SR signals during subsequent oscillations.

It is possible this cell autonomous behavior, which is likely not identifiable using cytoplasmic $Ca^{2+}$ traces alone, reflects the distinct stages of in vitro maturity. In support of this, a small proportion of stem-cell derived cardiomyocytes appear to develop a higher order structure to components such as SERCA™, which may be implicated in the excitation and contraction coupling was observed as shown in FIG. 13.

Observing $Ca^{2+}$ Dynamics in the Mitochondria

Figure 16:
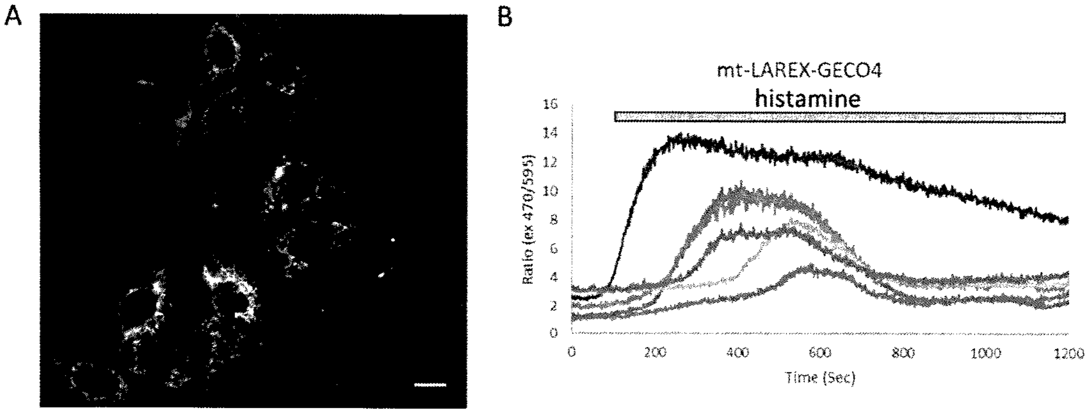
FIG. 16 shows that expression of mt-LAREX-GECO4 in Hela cells for ratiometric observing calcium dynamic in mitochondria. (A) Subcellular distribution of mt-LAREX-GECO4. Scale bar indicates 10 μm. (B) A huge $Ca^{2+}$ influx in mitochondria was detected in response to 20 μM histamine. mt-LAREX-GECO4 was excited by LED illumination at 470 nm and 595 nm. Histamine application is indicated by the gray bar.

It is known that calcium signaling plays an important role in regulating mitochondrial function. Mitochondrial calcium ($Ca^{2+}$) overload is one of the pro-apoptotic ways to induce the swelling of mitochondria. Thus, real-time monitoring $Ca^{2+}$ dynamics in prediction of cellular states or response to different stimulation would be of interest. However, like ER/SR, mitochondria also contain high concentrations of $Ca^{2+}$, and therefore there are relatively few variants optimized for use to study calcium signaling in mitochondria. The low affinity indicators of the present invention may provide a solution. FIG. 16 shows that expression of mt-LAREX-GECO4 in HeLa cells for ratiometric observing calcium dynamic in mitochondria. (A) Subcellular distribution of mt-LAREX-GECO4. Scale bar indicates 10 μm. (B) A huge $Ca^{2+}$ influx in mitochondria was detected in response to 20 μM histamine. mt-LAREX-GECO4 was excited by LED illumination at 470 nm and 595 nm. Histamine application is indicated by the gray bar.

Polypeptide and Nucleotide Sequences

Aspects of the invention include the fluorescent polypeptides described herein, having the amino acid sequences indicated, or a substantially similar amino acid sequence. A substantially similar amino acid sequence will have at least some level of sequence identity, with the same or similar function. It is well understood by one skilled in the art that many levels of sequence identity are useful in identifying polypeptides, wherein such polypeptides have the same or similar function or activity. Percent identities of 90% or greater (ie. 91%, 92%, 93%, 94%, 95%, 96%, 97%, 98% or 99%) may be useful.

In examples of the present invention, polypeptides will have the same or similar function if they are similarly fluorescent and have a low-affinity for $Ca^{2+}$, with a $K_d$ of greater than 20 μM, and more preferably greater than about 60 μM. However, it will be understood that the progenitor fluorescent polypeptides LAR-GECO1 and REX-GECO1 are not included as having substantially similar sequences, nor are any nucleic acid sequences which encode for the progenitor fluorescent polypeptides.

As used herein, "nucleic acid" means a polynucleotide and includes single or double-stranded polymer of deoxyribonucleotide or ribonucleotide bases. Nucleic acids may also include fragments and modified nucleotides. Thus, the terms "polynucleotide", "nucleic acid sequence", "nucleotide sequence" or "nucleic acid fragment" are used interchangeably and is a polymer of RNA or DNA that is single- or double-stranded, optionally containing synthetic, non-natural or altered nucleotide bases. Nucleotides (usually found in their 5'-monophosphate form) are referred to by their single letter designation as follows: "A" for adenylate or deoxyadenylate (for RNA or DNA, respectively), "C" for cytidylate or deosycytidylate, "G" for guanylate or deoxyguanylate, "U" for uridlate, "T" for deosythymidylate, "R" for purines (A or G), "Y" for pyrimidiens (C or T), "K" for G or T, "H" for A or C or T, "I" for inosine, and "N" for any nucleotide.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

The invention may also comprise a nucleic acid sequence encoding a polypeptide having an amino acid sequence described herein, or a substantially similar amino acid sequence, as well as substantially similar nucleic acid sequences. Substantially similar nucleic acid sequences may have 90% or greater sequence identity (i.e. 91%, 92%, 93%, 94%, 95%, 96%, 97%, 98% or 99%).

"Sequence identity" or "identity" in the context of nucleic acid or polypeptide sequences refers to the nucleic acid bases or amino acid residues in two sequences that are the same when aligned for maximum correspondence over a specified comparison window. Thus, "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. These identities can be determined by those skilled in the art, including the use of any of the programs described herein.

Sequence alignments and percent identity or similarity calculations may be determined using a variety of comparison methods designed to detect homologous sequences including, but not limited to, the MEGALIGN® sequence alignment program of the LASERGENE® bioinformatics computing suite (DNASTAR Inc.®, Madison, Wis.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, CABIOS. 5:151-153 (1989); Higgins, D. G. et al. (1992) Comput. Appl. Biosci. 8:189-191) and found in the MEGALIGN® sequence alignment program of the LASERGENE® bioinformatics computing suite (DNASTAR Inc.®, Madison, Wis.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

"BLASTN method of alignment" is an algorithm provided by the National Center for Biotechnology Information (NCBI®) to compare nucleotide sequences using default parameters.

Moreover, the skilled artisan recognizes that substantially similar nucleic acid sequences encompassed by this invention are also defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 85%, 90% or 95% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth et al., Anal. Biochem. 138:267-284 (1984): $T_m$=81.5° C.±16.6 (log M)+0.41 (% GC)-0.61 (% form)-500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4°

C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology-Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel et al., Eds., Greene Publishing and Wiley-Interscience, New York (1995). Hybridization and/or wash conditions can be applied for at least 10, 30, 60, 90, 120, or 240 minutes.

EXAMPLES

Embodiments of the present invention are described with reference to the following Examples. These Examples are provided for the purpose of illustration only.

Example 1A: Engineering of LAR-GECOs

LAR-GECO1 in pBAD/His B vector™ (LIFE TECHNOLOGIES®) was used as the initial template to assemble LAR-GECO1.5 (strategy 1-FIG. 1). The development of LAR-GECO1 is described in Wu et al. *Red fluorescent genetically encoded* $Ca^{2+}$ *indicators for use in mitochondria and endoplasmic reticulum*, Biochem J. 2014 Nov. 15; 464 (1): 13-22, the entire contents of which are incorporated herein by reference, where permitted.

The N-terminus of RS20 and the C-terminus of CaM in LAR-GECO1 were connected by a seven (7) amino acid sequence, while the original ncp FP termini were reinstated by overlap extension polymerase chain reactions (PCR). To explore strategies 2, 3, and 4, which led to the development of LAR-GECO2, 3, and 4, point mutations listed in Table 4 were introduced to LAR-GECO1.5 using Quikchange Lightning Site-Directed Mutagenesis Kit™ (AGILENT TECHNOLOGIES®) following manufacturer's instructions. Oligonucleotides containing specific mutations were designed in the aid of AGILENT® online mutagenesis primer design program.

TABLE 4

Summary of mutations introduced to engineer the LAR indicator series

| Strategy | Mutation | Comments |
|---|---|---|
| Strategy 2 Alanine-scanning through RS20-CaM interface | R41A | |
| | R42A | |
| | K43A | |
| | W44A | |
| | N45A | |
| | K46A | |
| | G48A | |
| | H49A | |
| | W51A | |
| | R52A | |
| | I54A | Designated as LAR-GECO2 |
| | R56A | |
| | L57A | |
| | E314A | |
| | L321A | |
| | F322A | |
| | M375A | |
| | E387A | |
| | M412A | |
| | E417A | |
| | M448A | |
| Strategy 3 CaM mutations from O-GECO1 and R-GECO1.2 | I330M | Designated as LAR-GECO3 |
| | K397N | Previously reported (Wu et al., 2013) |
| Strategy 4 Mutations in the EF-hands of CaM | T329D/ T365D/ D367N | Previously reported (Sun et al., 2013) |
| | T365D/ D367N | Previously reported (Sun et al., 2013) |
| | T329D/ T331D/ T365D | Previously reported (Sun et al., 2013) |
| | T363D | Previously reported (Sun et al., 2013) |
| | T329D/ T331D | Previously reported (Sun et al., 2013) |
| | D363N/ D367N | Previously reported (Sun et al., 2013) |
| | D327N/ I330M | Previously reported (Sun et al., 2013; Wu et al., 2013) |
| | D327N/ I330M/ D363N | Designated as LAR-GECO4 |
| | E334A | Previously reported (Sun et al., 2013) |
| | T365D | Previously reported (Sun et al., 2013) |

Example 1B: Engineering of LAREX-GECOS

To engineer LAREX-GECO1 and 2, REX-GECO1 in pBAD/His B vector (LIFE TECHNOLOGIES®) was first turned into the ncp topology by overlap extension PCR as described above. Point mutations from LAR-GECO3 and 4 were then introduced to this ncp version of REX-GECO1 using Quikchange Lightning Site-Directed Mutagenesis Kit (AGILENT TECHNOLOGIES®) as described above to make LAREX-GECO1 and 2 respectively. To construct LAREX-GECO3, the CaM domain of REX-GECO1 was replaced by the CaM domain of R-CEPIAler via overlap extension PCR. pCMV R-CEPIAler™ was a gift from Masamitsu Iino™ (Addgene plasmid #58216). LAREX-GECO4 was constructed by changing the topology of LAREX-GECO3 to ncp as described above. The sequence of all the LAR-GECO and LAREX-GECO constructs was verified by sequencing.

To test the $Ca^{2+}$ affinity of all the LAR-GECO and LAREX-GECO variants, each variant in pBAD/His B vector (Life Technologies) was electroporated into *E. coli* strain DH10B™ (INVITROGEN®). *E. coli* containing these variants were then cultured on 10 cm LB-agar Petri dishes supplemented with 400 μg/mL ampicillin (SIGMA-ALDRICH®) and 0.02% (wt/vol) L-arabinose (ALFA AESAR®) at 37° C. overnight. These Petri dishes were then placed at room temperature for 24 h before imaging. During imaging, an image was captured for each Petri dish by using excitation filter of 542/27 nm (for LAR-GECO variants), or both 438/24 nm and 542/27 nm (for LAREX-GECO variants) to illuminate *E. coli* colonies and emission filter of 609/57 nm. A single *E. coli* colony emitting red fluorescence of each variant was then picked and cultured in 4 mL liquid LB with 100 μg/mL ampicillin and 0.02% (wt/vol) L-arabinose at 37° C. overnight. Proteins were then extracted from the liquid LB culture by B-PER™ (PIERCE BIOTECHNOLOGY®) following manufacturer's instructions. The extracted protein solution of each variant was then subjected to $Ca^{2+}$ titration. In the $Ca^{2+}$ titration, extracted protein solutions were added into $Ca^{2+}$ buffers with different free $Ca^{2+}$ concentrations. $Ca^{2+}$/HEDTA, and $Ca^{2+}$/NTA buffers were prepared by mixing $Ca^{2+}$-saturated and $Ca^{2+}$-free buffers (30 mM MOPS, 100 mM KCl, 10 mM chelating reagent, pH 7.2, either with or without 10 mM $Ca^{2+}$) to achieve the buffer $Ca^{2+}$ concentrations from 0 mM to 1.3 mM. Fluorescence spectra of each variant in different $Ca^{2+}$ concentrations were recorded by using a Safire2™ fluorescence microplate reader (TECAN®). These fluorescence intensities were then plotted against $Ca^{2+}$ concentrations and fitted by Hill equation to calculate the dissociation constant to $Ca^{2+}$ of each variant.

Example 2: In Vitro Characterization

For detailed characterization of LAR-GECOs, proteins were expressed and purified as described in Wu J, Liu L, Matsuda T, Zhao Y, Rebane A, Drobizhev M, et al. *Improved orange and red $Ca^{2+}$indicators and photophysical considerations for optogenetic applications*. ACS Chem Neurosci. 2013; 4:963-972 (Wu et al. 2013). Spectral measurements were performed in solutions containing 10 mM EGTA or 10 mM CaNTA, 30 mM MOPS, 100 mM KCl, pH 7.2. For determination of fluorescence quantum yield of LAR-GECOs and LAREX-GECOS, mCherry and LSS-mKate2 were used as standards. Procedures for measurement of fluorescence quantum yield, extinction coefficient, $pK_a$, $K_d$ for $Ca^{2+}$ have been described in Wu et al. 2013. For $Ca^{2+}$ titration, purified proteins were added into $Ca^{2+}$/HEDTA, and $Ca^{2+}$/NTA buffers, and fluorescence measurements were performed as described above.

Figure 5:
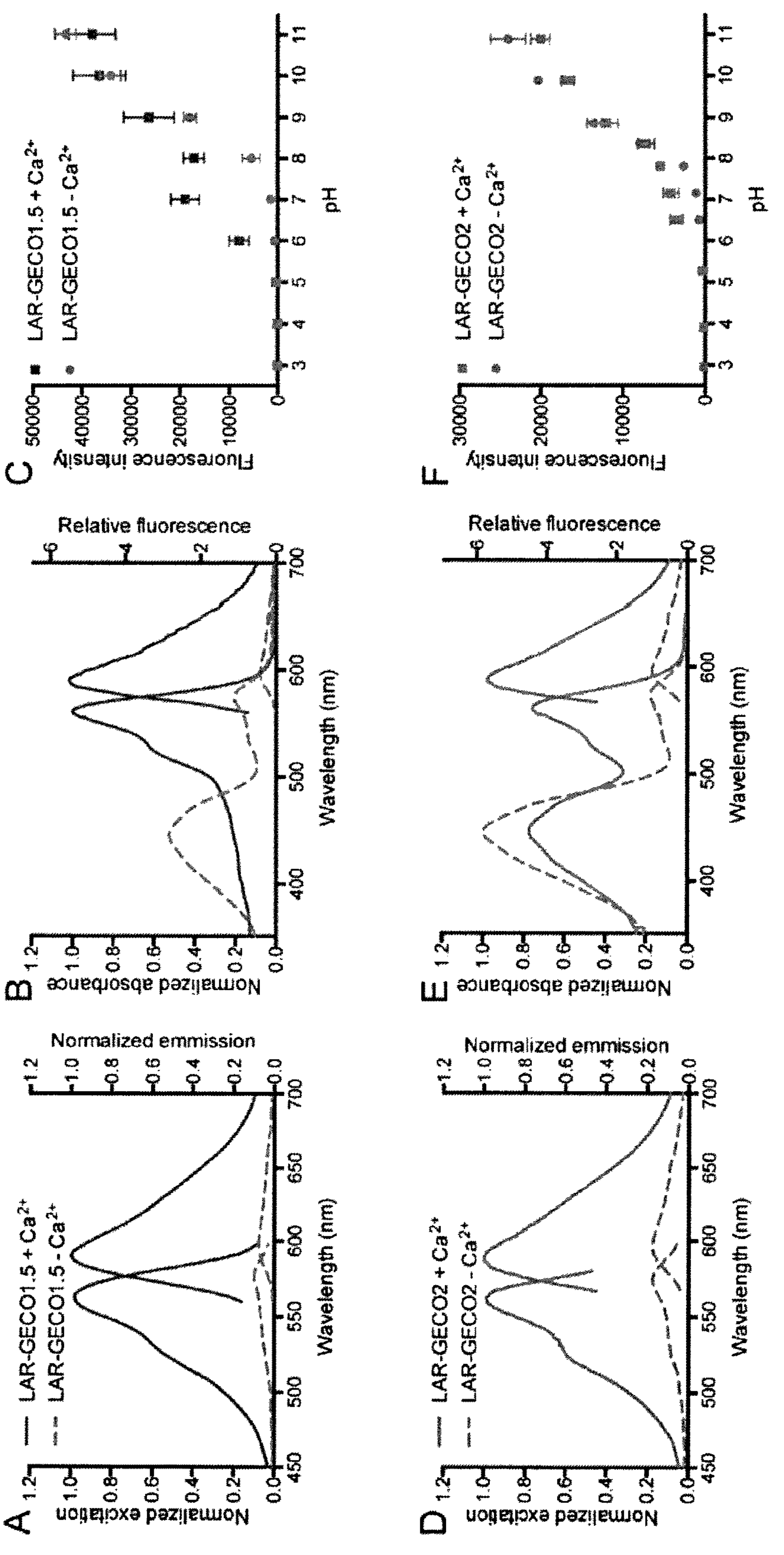
FIG. 5 shows in vitro characterizations of LAR-GECOs. (A, D, G and J) Excitation and emission spectra of LAR-GECO1.5 (A), LAR-GECO2 (D), LAR-GECO3 (G), and LAR-GECO4 (J). (B, E, H and K) Absorbance and emission spectra of LAR-GECO1.5 (B), LAR-GECO2 (E), LAR-GECO3 (H), and LAR-GECO4 (K) in both the $Ca^{2+}$-free state (dotted line) and the $Ca^{2+}$-bound state (solid line). (C, F, I, L) Fluorescence intensity of LAR-GECO1.5 (C), LAR-GECO2 (F), LAR-GECO3 (I), and LAR-GECO4 (L) as a function of pH.
Figure 5:
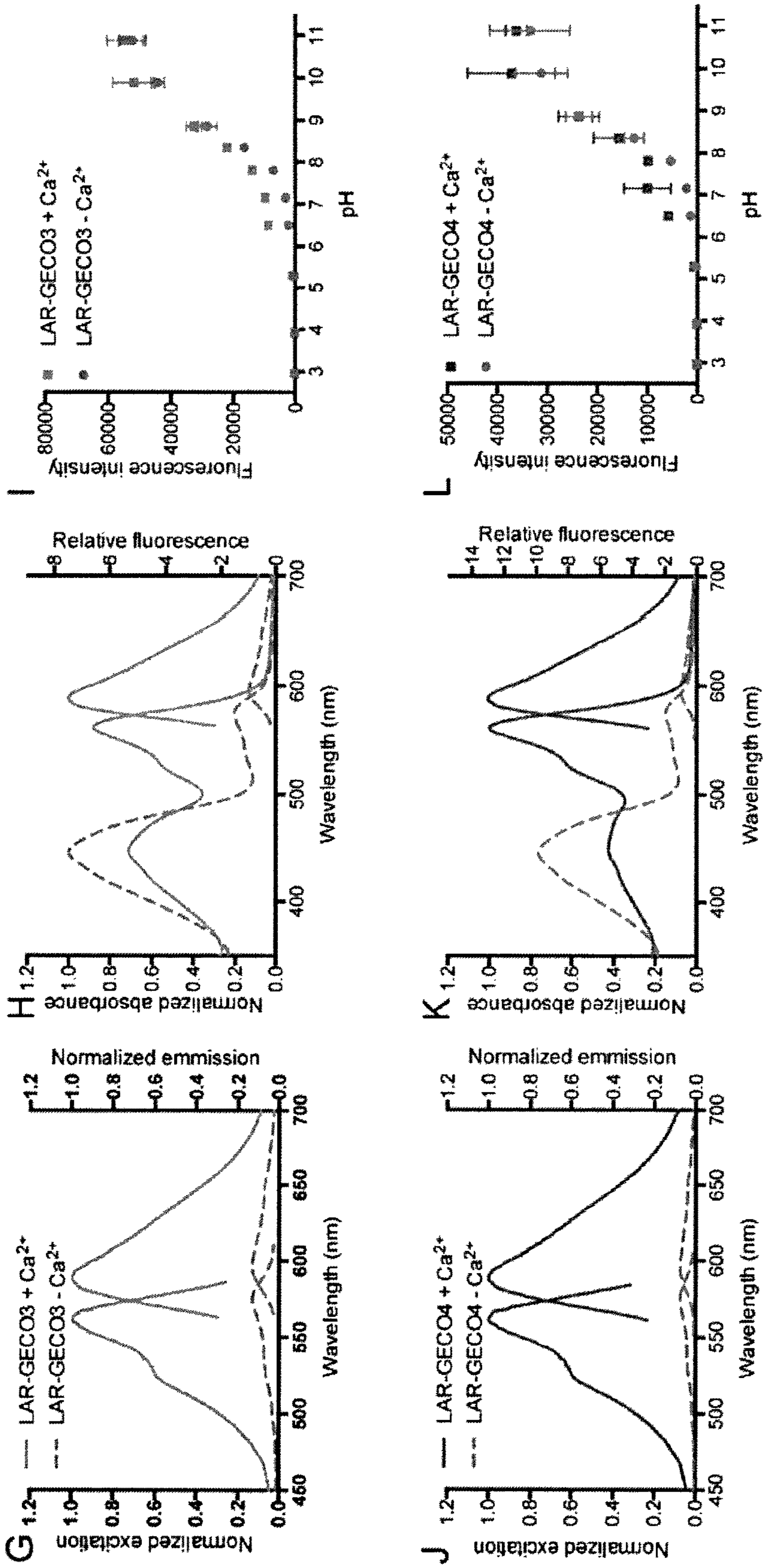

With reference to FIG. 5, in vitro characterization of LAR-GECO1.5, LAR-GECO2, LAR-GECO3, and LAR-GECO4 shows that all four ncp $Ca^{2+}$ indicators share substantially identical spectral properties with their progenitor, LAR-GECO1. In addition, these new LAR-GECOs exhibit a similar monophasic dependence on pH in the $Ca^{2+}$ free state. Upon binding to $Ca^{2+}$, this dependence on pH switches from monophasic to biphasic, which is very similar to LAR-GECO1's pH dependence.

With reference to FIG. 6, the new LAREX-GECOs share very similar spectral properties with their progenitor, REX-GECO1. Furthermore, these LAREX-GECOs display a similar pH dependence profile with REX-GECO1, with the largest $Ca^{2+}$-dependent change in ratio occurring between pH 7 to 9.

Example 3: Plasmids for Mammalian Cell Imaging

The ER targeted GECO genes were generated using primers containing ER targeting sequence (MLLPVPLLLGLLGAAAD [SEQ ID NO. 19]) and an ER retention signal sequence as known in the art. The PCR products were subjected to digestion with the BamHI™ and EcoRI™ restriction enzymes (THERMO FISHER SCIENTIFIC®). The digested DNA fragments were ligated with a modified pcDNA3 plasmid that had previously been digested with the same two enzymes. Plasmid were purified with the GeneJET miniprep kit™ (THERMO FISHER SCIENTIFIC®) and then sequenced to verify the inserted genes.

Example 4: Cell Culture Conditions and Transfection

To culture the HL1 cell line, flasks were pre-coated with gelatin/fibronectin at 37° C. overnight. Cells were cultured in supplemented Claycomb Medium™ (Claycomb Medium with 10% fetal bovine serum (SIGMA-ALDRICH® 12103C (Batch 8A0177)), 1 U/ml penicillin/streptomycin, 0.1 mM norepinephrine and 2 mM L-glutamine) and split 1:3 when they reached confluency. Cells were transfected using transfection reagent, Lipofectamine 2000 (INVITROGEN®), for 48 hours before acquiring images.

The OxF2 human embryonic stem cell line was cultured on mouse embryonic fibroblasts (MEF) in ES medium containing DMEM/F12™ (INVITROGEN®), 20% Knockout Serum Replacer™ (KSR, INVITROGEN®), 1 mM glutamine, 1% non-essential amino acids, 125 μM mercaptoethanol, 0.625% penicillin/streptomycin and 4 ng/ml basic Fibroblast Growth Factor (bFGF) (Peprotech). One week before differentiation, ES colonies were manually cut and placed on Geltrex™ (GIBCO®) coated six-well plates in mTeSR1 medium™ (STEMCELL TECHNOLOGIES®).

Human iPSC-derived cardiomyocytes (Human iPSC Cardiomyocytes-Malel ax2505™) were bought from Axol Bioscience. The cells were plated in two wells of 6-well plate and cultured for eight days in Axol's Cardiomyocyte Maintenance Medium™ to 80-90% confluency. Cells then were replated on Fibronectin/Gelatin (0.5%/0.1%) coated glass bottom dishes, and were transfected using transfection reagent, Lipofectamine 2000 (INVITROGEN®). Tyrode's buffer was used for final observation.

HeLa cells were cultured in homemade 35-mm glass-bottom dishes in Dulbecco's modified Eagle medium (SIGMA-ALDRICH®) containing 10% fetal bovine serum (INVITROGEN®). Cells were transfected with CMV-mito-LAREX-GECO4, ER-LAREX-GECO3 and ER-LAREX-GECO4 using a transfection reagent of Lipofectamine 2000 (INVITROGEN®).

Example 5: Cardiomyocyte Differentiation from Human Pluripotent Stem Cells

This protocol is based on method reported in Lian X, Zhang J, Azarin S M, Zhu K, Hazeltine L B, Bao X, et al. *Directed cardiomyocyte differentiation from human pluripotent stem cells by modulating Wnt/β-catenin signaling under fully defined conditions*. Nat Protoc. 2013; 8:162-175. ES cell colonies were dissociated into single cells using accutase and put into 6-well plates coated with Geltrex at $0.5\times10^6$ cells per well, in mTeSR1 with added rock inhibitor, Y27632 (10 μM). On day 3, at 80-90% confluence, medium was changed to RPMI/B27 (B27 supplement without insulin-GIBCO®) containing 12 μM GSK-3 inhibitor, CHIR 99021Tocris™). After 24 hours, medium was changed to remove CHIR. 48 hours later, half the medium (1 ml) from each well was aspirated and replaced with fresh RPMI/B27 containing a final concentration of 5 μM wnt inhibitor, IWP 2™ (TOCRIS BIOSCIENCE®). 48 hours later the IWP was removed and after a further 48 hours the medium was changed to RPMI+B27™ with insulin (GIBCO®). Cultures were maintained in this medium, which was changed twice weekly. Cells then were replated on Fibronectin/Gelatin (0.5%/0.1%) coated glass bottom dishes, and were transfected using transfection reagent, Lipofectamine 2000 (INVITROGEN®).

Example 6: Immunostaining for Characterization of hES Derived Cardiomyocytes

Primary antibodies were mouse monoclonal anti-actinin (SIGMA-ALDRICH® no. A7811) rabbit polyclonal anti-troponin I (ABCAM®, ab47003) and mouse monoclonal anti-SERCA2 ATPase™ (AUSTRALIAN BIORESOURCES® no MA3-910). Secondary antibodies were Fab fragment anti-mouse 488 and anti-rabbit 568™ (MOLECULAR PROBES®). The procedure was as follows: 4% paraformaldehyde fixation (10 min room temperature), 0.1% Triton x-100 in Tris-buffered saline (TBST) to permeabilize and wash, 2% BSA with 0.001% sodium azide in TBST for blocking (1 hr room temperature), primary antibodies at 1:200 (2 hr room temperature), 3× wash with TBST (5 mins per wash), secondary antibodies 1:1000 (1 hr room temperature), 3× wash with TBST (5 mins per wash), dry the coverslip and mount in Vectorshield™ (VECTOR LABORATORIES®). Fluorescence imaging was done with a Leica SP5 confocal microscope using a 63× oil lens with 488 nm and 543 nm excitation.

Example 7: Live Cell Imaging Conditions

For non-ratiometric imaging, an inverted microscope (IX81™, Olympus) equipped with a 60× objective lens (NA 1.42™, Olympus) and a multiwavelength LED light source (OptoLED™, CARIN) was used. Blue (470 nm) and green (550 nm) excitation were used to illuminate G-GECO or G-CEPIA and LAR-GECOs, respectively. The GFP filter set (DS/FF02-485/20-25, T4951pxr dichroic mirror, and ET525/50 emission filter) was used to observe G-GECO signal in HL1 cells. The RFP filter set (DS/FF01-560/25-25, T5651pxr dichroic mirror, and ET620/60 emission filter) was used to observe signal of LAR-GECO3 and LAR-GECO4 in HL1 cells. A quad-band filter set including a quad-band bandpass filter (DS/FF01-387/485/559/649-25, Semrock), dichroic quad-edge beamsplitter (DS/FF410/504/582/669-Di01-25x36™, Semrock) and a quad-band bandpass emission filter (DS/FF01-440/521/607/700-25™, Semrock) was used to simultaneously observe G-CEPIA and LAR-GECOs or G-GECO and LAR-GECOs in ES-CMs. Fluorescence signals were recorded through Dual-View system (DC2™, PHOTOMETRICS®) with green (520/30 nm) and red (630/50 nm) channels to EM-CCD cameras (ImagEM™, HAMAMATSU PHOTONICS®) controlled by software (CellR™, OLYMPUS CORPORATION®).

For ratiometric imaging of HL1 cells, ES-CMs and iPS-CMs by LAREX-GECOs, an inverted confocal microscope ZEISS® LSM710™, equipped with 63× 1.40 NA oil objective and multi-argon ion laser was used. In HL1 cells, images of red fluorescence and far red signals of LAREX-GECOs were detected at 560-710 nm, and 630-720 nm wavelength range, respectively, using 488 nm excitation and 594 nm excitation. For simultaneous ratiometric ER and cytoplasmic $Ca^{2+}$ transients in iPS-CMs, green, red and far red signals were detected at 492-540 nm, 630-728 nm, and 630-728 nm wavelength range, respectively, using 488 nm excitation and 594 nm excitation.

For ratiometric imaging in HeLa cells (FIGS. 7 and 16) and iPSC-CMs (FIG. 14), An inverted microscope (D1, ZEISS®) equipped with a 63× objective lens (NA 1.4, Zeiss) and a multiwavelength LED light source (pE-4000, COOLLED®) was used. Blue (470 nm) and orange (595 nm) excitation were used to illuminate LAREX-GECOs for ratiometric excitation. The RFP filter set (T5901pxr dichroic mirror, and ET 590lp emission filter) was used to imaging of LAREXs. Fluorescence signals were recorded using a CMOS camera (ORCA-Flash4.0LT, HAMAMATSU PHOTONICS®) controlled by a software (HC Image).

Example 8: Construction of CMV-Mito-LAREX-GECO4 Vector

LAREX-GECO4 were subcloned from pcDNA3-LAREX-GECO4 (without ER targeting and retention sequence) as follow: PCR primers with a 5' BamHI linker (MT-BamHI-LAREX_GECO4-F) and a 3' HindIII linker (MT-HindIII-LAREX-GECO4-R) were used to amplify LAREX-GECO4 that do not containing ER targeting (MLLPVPLLLGLLGAAAD [SEQ ID NO. 19]) and retention sequences from pcDNA3-LAREX-GECO4 plasmid and ligated with BamHI, HindIII-digested CMV-mito-LAR-GECO1.2 (Addgene #61245) to replace LAR-GECO1.2 fragment. A start codon (ATG) were added to replace ER targeting sequences and a stop codon (TAA) were added in place of retention sequences.

Oligonucleotides used in the cloning steps are, MT-BamHI-LAREX GECO4-F: 5'-GATCGGATCCAACCATGGTGAGCAAGGGCGAGGAGGAT-3' [SEQ ID NO. 20] and MT-HindIII-LAREX GECO4-R: 5'-GATCAAGCTTTTACTTGTACAGCTCGTCCATGCC-3' [SEQ ID NO. 21].

Interpretation

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated. To the extent that the following description is of a specific embodiment or a particular use of the invention, it is intended to be illustrative only, and not limiting of the claimed invention.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to combine, affect or connect such aspect, feature, structure, or characteristic with other embodiments, whether or not such connection or combination is explicitly described. In other words, any element or feature may be combined with any other element or feature in different embodiments, unless there is an obvious or inherent incompatibility between the two, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, any range discussed herein can be readily broken down into a lower third, middle third and upper third, etc.

As will also be understood by one skilled in the art, all ranges described herein, and all language such as "up to", "at least", "greater than", "less than", "more than", "or more", and the like, include the number(s) recited and such terms refer to ranges that can be subsequently broken down into sub-ranges as discussed above.

The invention claimed is:

1. A low affinity fluorescent $Ca^{2+}$ polypeptide comprising a sequence selected from the group consisting of: SEQ ID Nos: 12, 14, and 18, which is fluorescent and has an affinity for $Ca^{2+}$ with a $K_d$ of greater than 20 μM.

2. The polypeptide of claim 1 having a $K_d$ for $Ca^{2+}$ greater than 60 M.

3. The polypeptide of claim 1, further comprising an endoplasmic reticulum (ER) targeting sequence of SEQ ID NO: 19.

* * * * *

SEQUENCE LISTING

<160> NUMBER OF SEQ ID NOS: 21

<210> SEQ ID NO 1
<211> LENGTH: 1251
<212> TYPE: DNA
<213> ORGANISM: Homo sapiens

<400> SEQUENCE: 1
atggtcgact cttcacgtcg taagtggaat aaggcaggtc acgcatggag agctataggt 60
cggctgagct cacccgtggt ttccgagcgg atgtaccccg aggacggagc cctgaagagc 120
gagatcaaga aggggctgag gctgaaggac ggcggccact acgccgccga ggtcaagacc 180
acctacaagg ccaagaagcc cgtgcagctg cccggcgcct acgtcgtcga catcaagttg 240
gacatcgtgt cccacaacga ggactacacc atcgtggaac agtgcgaacg cgccgagggc 300
cgccactcca ccggcggcat ggacgagctg tacaagggag gtacaggcgg gagtctggtg 360
agcaagggcg aggaggataa catggccatc atcaaggagt tcatgcgctt caaggtgcac 420
atggagggct ccgtgaacgg ccacgagttc gagatcgagg gcgagggcga gggccgcccc 480
tacgaggcct ttcagaccgc taagctgaag gtgaccaagg gtggcccct gcccttcgcc 540 tgggacatcc tgtcccctca gttcatgtac ggctccaagg cctacattaa gcacccagcc 600
gacatccccg actacttcaa gctgtccttc cccgagggct tcaggtggga gcgcgtgatg 660
aacttcgagg acggcggcat tattcacgtt aaccaggact cctccctgca ggacggcgta 720
ttcatctaca aggtgaagct gcgcggcacc aacttccccc ccgacggccc cgtaatgcag 780
aagaagacca tgggctggga ggctacgcgc gaccaactga ctgaagagca gatcgcagaa 840
tttaaagagg ctttctccct atttgacaag gacggggatg ggacgataac aaccaaggag 900
ctggggacgg tgatgcggtc tctggggcag aaccccacag aagcagagct gcaggacatg 960
atcagtgaag tagatgccga cggtgacggc acattcgact tccctgagtt cctgacgatg 1020
atggcaagaa aaatgaatta cacagacagt gaagaggaaa ttagagaagc gttccgcgtg 1080
gcggataagg acggcaatgg ctacatcggc gcagcagagc ttcgccacgc gatgacagac 1140
attggagaga agttaacaga tgaggaggtt gatgaaatga tcagggtagc agacatcgat 1200
ggggatggtc aggtaaacta cgaagagttt gtacaaatga tgacagcgaa g 1251

<210> SEQ ID NO 2

<211> LENGTH: 417
<212> TYPE: PRT
<213> ORGANISM: Homo sapiens

<400> SEQUENCE: 2

```
Met Val Asp Ser Ser Arg Arg Lys Trp Asn Lys Ala Gly His Ala Trp
1               5                   10                  15

Arg Ala Ile Gly Arg Leu Ser Ser Pro Val Val Ser Glu Arg Met Tyr
            20                  25                  30

Pro Glu Asp Gly Ala Leu Lys Ser Glu Ile Lys Lys Gly Leu Arg Leu
        35                  40                  45

Lys Asp Gly Gly His Tyr Ala Ala Glu Val Lys Thr Thr Tyr Lys Ala
    50                  55                  60

Lys Lys Pro Val Gln Leu Pro Gly Ala Tyr Val Val Asp Ile Lys Leu
65                  70                  75                  80

Asp Ile Val Ser His Asn Glu Asp Tyr Thr Ile Val Glu Gln Cys Glu
                85                  90                  95

Arg Ala Glu Gly Arg His Ser Thr Gly Gly Met Asp Glu Leu Tyr Lys
            100                 105                 110

Gly Gly Thr Gly Gly Ser Leu Val Ser Lys Gly Glu Glu Asp Asn Met
        115                 120                 125

Ala Ile Ile Lys Glu Phe Met Arg Phe Lys Val His Met Glu Gly Ser
    130                 135                 140

Val Asn Gly His Glu Phe Glu Ile Glu Gly Glu Gly Glu Gly Arg Pro
145                 150                 155                 160

Tyr Glu Ala Phe Gln Thr Ala Lys Leu Lys Val Thr Lys Gly Gly Pro
                165                 170                 175

Leu Pro Phe Ala Trp Asp Ile Leu Ser Pro Gln Phe Met Tyr Gly Ser
            180                 185                 190

Lys Ala Tyr Ile Lys His Pro Ala Asp Ile Pro Asp Tyr Phe Lys Leu
        195                 200                 205

Ser Phe Pro Glu Gly Phe Arg Trp Glu Arg Val Met Asn Phe Glu Asp
    210                 215                 220

Gly Gly Ile Ile His Val Asn Gln Asp Ser Ser Leu Gln Asp Gly Val
225                 230                 235                 240

Phe Ile Tyr Lys Val Lys Leu Arg Gly Thr Asn Phe Pro Pro Asp Gly
                245                 250                 255

Pro Val Met Gln Lys Lys Thr Met Gly Trp Glu Ala Thr Arg Asp Gln
            260                 265                 270

Leu Thr Glu Glu Gln Ile Ala Glu Phe Lys Glu Ala Phe Ser Leu Phe
        275                 280                 285

Asp Lys Asp Gly Asp Gly Thr Ile Thr Thr Lys Glu Leu Gly Thr Val
    290                 295                 300

Met Arg Ser Leu Gly Gln Asn Pro Thr Glu Ala Glu Leu Gln Asp Met
305                 310                 315                 320

Ile Ser Glu Val Asp Ala Asp Gly Asp Gly Thr Phe Asp Phe Pro Glu
                325                 330                 335

Phe Leu Thr Met Met Ala Arg Lys Met Asn Tyr Thr Asp Ser Glu Glu
            340                 345                 350

Glu Ile Arg Glu Ala Phe Arg Val Ala Asp Lys Asp Gly Asn Gly Tyr
        355                 360                 365

Ile Gly Ala Ala Glu Leu Arg His Ala Met Thr Asp Ile Gly Glu Lys
    370                 375                 380

Leu Thr Asp Glu Glu Val Asp Glu Met Ile Arg Val Ala Asp Ile Asp
```

```
385                 390                 395                 400

Gly Asp Gly Gln Val Asn Tyr Glu Glu Phe Val Gln Met Met Thr Ala
                405                 410                 415

Lys
```

<210> SEQ ID NO 3
<211> LENGTH: 1254
<212> TYPE: DNA
<213> ORGANISM: Homo sapiens

<400> SEQUENCE: 3

```
atggggagtc tggtgagcaa gggcgaggag gataacatgg ccatcatcaa ggagttcatg      60

cgcttcaagg tgcacatgga gggctccgtg aacggccacg agttcgagat cgagggcgag     120

ggcgagggcc gcccctacga ggcctttcag accgctaagc tgaaggtgac caagggtggc     180

cccctgccct tcgcctggga catcctgtcc cctcagttca tgtacggctc caaggcctac     240

attaagcacc cagccgacat ccccgactac ttcaagctgt ccttccccga gggcttcagg     300

tgggagcgcg tgatgaactt cgaggacggc ggcattattc acgttaacca ggactcctcc     360

ctgcaggacg gcgtattcat ctacaaggtg aagctgcgcg gcaccaactt cccccccgac     420

ggccccgtaa tgcagaagaa gaccatgggc tgggaggcta cgcgcgacca actgactgaa     480

gagcagatcg cagaatttaa agaggctttc tccctatttg acaaggacgg ggatgggacg     540

ataacaacca aggagctggg gacggtgatg cggtctctgg ggcagaaccc cacagaagca     600

gagctgcagg acatgatcag tgaagtagat gccgacggtg acggcacatt cgacttccct     660

gagttcctga cgatgatggc aagaaaaatg aattacacag acagtgaaga ggaaattaga     720

gaagcgttcc gcgtggcgga taaggacggc aatggctaca tcggcgcagc agagcttcgc     780

cacgcgatga cagacattgg agagaagtta acagatgagg aggttgatga aatgatcagg     840

gtagcagaca tcgatgggga tggtcaggta aactacgaag agtttgtaca aatgatgaca     900

gcgaagggtg gcggaggttc tgtcgactca tcacgtcgta agtggaataa ggcaggtcac     960

gcatggagag ctataggtcg gctgagctca cccgtggttt ccgagcggat gtaccccgag    1020

gacggagccc tgaagagcga gatcaagaag gggctgaggc tgaaggacgg cggccactac    1080

gccgccgagg tcaagaccac ctacaaggcc aagaagcccg tgcagctgcc cggcgcctac    1140

gtcgtcgaca tcaagttgga catcgtgtcc cacaacgagg actacaccat cgtggaacag    1200

tgcgaacgcg ccgagggccg ccactccacc ggcggcatgg tcgggctgta caag          1254
```

<210> SEQ ID NO 4
<211> LENGTH: 418
<212> TYPE: PRT
<213> ORGANISM: Homo sapiens

<400> SEQUENCE: 4

```
Met Gly Ser Leu Val Ser Lys Gly Glu Glu Asp Asn Met Ala Ile Ile
1               5                   10                  15

Lys Glu Phe Met Arg Phe Lys Val His Met Glu Gly Ser Val Asn Gly
            20                  25                  30

His Glu Phe Glu Ile Glu Gly Glu Gly Glu Gly Arg Pro Tyr Glu Ala
        35                  40                  45

Phe Gln Thr Ala Lys Leu Lys Val Thr Lys Gly Gly Pro Leu Pro Phe
    50                  55                  60

Ala Trp Asp Ile Leu Ser Pro Gln Phe Met Tyr Gly Ser Lys Ala Tyr
65                  70                  75                  80
```

```
Ile Lys His Pro Ala Asp Ile Pro Asp Tyr Phe Lys Leu Ser Phe Pro
                85                  90                  95

Glu Gly Phe Arg Trp Glu Arg Val Met Asn Phe Glu Asp Gly Gly Ile
            100                 105                 110

Ile His Val Asn Gln Asp Ser Ser Leu Gln Asp Gly Val Phe Ile Tyr
        115                 120                 125

Lys Val Lys Leu Arg Gly Thr Asn Phe Pro Pro Asp Gly Pro Val Met
    130                 135                 140

Gln Lys Lys Thr Met Gly Trp Glu Ala Thr Arg Asp Gln Leu Thr Glu
145                 150                 155                 160

Glu Gln Ile Ala Glu Phe Lys Glu Ala Phe Ser Leu Phe Asp Lys Asp
                165                 170                 175

Gly Asp Gly Thr Ile Thr Thr Lys Glu Leu Gly Thr Val Met Arg Ser
            180                 185                 190

Leu Gly Gln Asn Pro Thr Glu Ala Glu Leu Gln Asp Met Ile Ser Glu
        195                 200                 205

Val Asp Ala Asp Gly Asp Gly Thr Phe Asp Phe Pro Glu Phe Leu Thr
    210                 215                 220

Met Met Ala Arg Lys Met Asn Tyr Thr Asp Ser Glu Glu Glu Ile Arg
225                 230                 235                 240

Glu Ala Phe Arg Val Ala Asp Lys Asp Gly Asn Gly Tyr Ile Gly Ala
                245                 250                 255

Ala Glu Leu Arg His Ala Met Thr Asp Ile Gly Glu Lys Leu Thr Asp
            260                 265                 270

Glu Glu Val Asp Glu Met Ile Arg Val Ala Asp Ile Asp Gly Asp Gly
        275                 280                 285

Gln Val Asn Tyr Glu Glu Phe Val Gln Met Met Thr Ala Lys Gly Gly
    290                 295                 300

Gly Gly Ser Val Asp Ser Ser Arg Arg Lys Trp Asn Lys Ala Gly His
305                 310                 315                 320

Ala Trp Arg Ala Ile Gly Arg Leu Ser Ser Pro Val Val Ser Glu Arg
                325                 330                 335

Met Tyr Pro Glu Asp Gly Ala Leu Lys Ser Glu Ile Lys Lys Gly Leu
            340                 345                 350

Arg Leu Lys Asp Gly Gly His Tyr Ala Ala Glu Val Lys Thr Thr Tyr
        355                 360                 365

Lys Ala Lys Lys Pro Val Gln Leu Pro Gly Ala Tyr Val Val Asp Ile
    370                 375                 380

Lys Leu Asp Ile Val Ser His Asn Glu Asp Tyr Thr Ile Val Glu Gln
385                 390                 395                 400

Cys Glu Arg Ala Glu Gly Arg His Ser Thr Gly Gly Met Val Gly Leu
                405                 410                 415

Tyr Lys
```

<210> SEQ ID NO 5
<211> LENGTH: 1254
<212> TYPE: DNA
<213> ORGANISM: Homo sapiens

<400> SEQUENCE: 5

```
atggggagtc tggtgagcaa gggcgaggag gataacatgg ccatcatcaa ggagttcatg      60

cgcttcaagg tgcacatgga gggctccgtg aacggccacg agttcgagat cgagggcgag     120

ggcgagggcc gcccctacga ggcctttcag accgctaagc tgaaggtgac caagggtggc     180
```

```
cccctgccct tcgcctggga catcctgtcc cctcagttca tgtacggctc caaggcctac    240
attaagcacc cagccgacat ccccgactac ttcaagctgt ccttccccga gggcttcagg    300
tgggagcgcg tgatgaactt cgaggacggc ggcattattc acgttaacca ggactcctcc    360
ctgcaggacg gcgtattcat ctacaaggtg aagctgcgcg gcaccaactt cccccccgac    420
ggccccgtaa tgcagaagaa gaccatgggc tgggaggcta cgcgcgacca actgactgaa    480
gagcagatcg cagaatttaa agaggctttc tccctatttg acaaggacgg ggatgggacg    540
ataacaacca aggagctggg gacggtgatg cggtctctgg ggcagaaccc cacagaagca    600
gagctgcagg acatgatcag tgaagtagat gccgacggtg acggcacatt cgacttccct    660
gagttcctga cgatgatggc aagaaaaatg aattacacag acagtgaaga ggaaattaga    720
gaagcgttcc gcgtggcgga taaggacggc aatggctaca tcggcgcagc agagcttcgc    780
cacgcgatga cagacattgg agagaagtta acagatgagg aggttgatga aatgatcagg    840
gtagcagaca tcgatgggga tggtcaggta aactacgaag agtttgtaca aatgatgaca    900
gcgaagggtg gcggaggttc tgtcgactca tcacgtcgta agtggaataa ggcaggtcac    960
gcatggagag ctgcaggtcg gctgagctca cccgtggttt ccgagcggat gtaccccgag   1020
gacggagccc tgaagagcga gatcaagaag gggctgaggc tgaaggacgg cggccactac   1080
gccgccgagg tcaagaccac ctacaaggcc aagaagcccg tgcagctgcc cggcgcctac   1140
gtcgtcgaca tcaagttgga catcgtgtcc cacaacgagg actacaccat cgtggaacag   1200
tgcgaacgcg ccgagggccg ccactccacc ggcggcatgg tcgggctgta caag         1254
```

```
<210> SEQ ID NO 6
<211> LENGTH: 418
<212> TYPE: PRT
<213> ORGANISM: Homo sapiens

<400> SEQUENCE: 6

Met Gly Ser Leu Val Ser Lys Gly Glu Glu Asp Asn Met Ala Ile Ile
1               5                   10                  15

Lys Glu Phe Met Arg Phe Lys Val His Met Glu Gly Ser Val Asn Gly
            20                  25                  30

His Glu Phe Glu Ile Glu Gly Glu Gly Glu Gly Arg Pro Tyr Glu Ala
        35                  40                  45

Phe Gln Thr Ala Lys Leu Lys Val Thr Lys Gly Gly Pro Leu Pro Phe
    50                  55                  60

Ala Trp Asp Ile Leu Ser Pro Gln Phe Met Tyr Gly Ser Lys Ala Tyr
65                  70                  75                  80

Ile Lys His Pro Ala Asp Ile Pro Asp Tyr Phe Lys Leu Ser Phe Pro
                85                  90                  95

Glu Gly Phe Arg Trp Glu Arg Val Met Asn Phe Glu Asp Gly Gly Ile
            100                 105                 110

Ile His Val Asn Gln Asp Ser Ser Leu Gln Asp Gly Val Phe Ile Tyr
        115                 120                 125

Lys Val Lys Leu Arg Gly Thr Asn Phe Pro Pro Asp Gly Pro Val Met
    130                 135                 140

Gln Lys Lys Thr Met Gly Trp Glu Ala Thr Arg Asp Gln Leu Thr Glu
145                 150                 155                 160

Glu Gln Ile Ala Glu Phe Lys Glu Ala Phe Ser Leu Phe Asp Lys Asp
                165                 170                 175

Gly Asp Gly Thr Ile Thr Thr Lys Glu Leu Gly Thr Val Met Arg Ser
```

```
            180                 185                 190

Leu Gly Gln Asn Pro Thr Glu Ala Glu Leu Gln Asp Met Ile Ser Glu
        195                 200                 205

Val Asp Ala Asp Gly Asp Gly Thr Phe Asp Phe Pro Glu Phe Leu Thr
    210                 215                 220

Met Met Ala Arg Lys Met Asn Tyr Thr Asp Ser Glu Glu Glu Ile Arg
225                 230                 235                 240

Glu Ala Phe Arg Val Ala Asp Lys Asp Gly Asn Gly Tyr Ile Gly Ala
                245                 250                 255

Ala Glu Leu Arg His Ala Met Thr Asp Ile Gly Glu Lys Leu Thr Asp
            260                 265                 270

Glu Glu Val Asp Glu Met Ile Arg Val Ala Asp Ile Asp Gly Asp Gly
        275                 280                 285

Gln Val Asn Tyr Glu Glu Phe Val Gln Met Met Thr Ala Lys Gly Gly
    290                 295                 300

Gly Gly Ser Val Asp Ser Ser Arg Arg Lys Trp Asn Lys Ala Gly His
305                 310                 315                 320

Ala Trp Arg Ala Ala Gly Arg Leu Ser Ser Pro Val Val Ser Glu Arg
                325                 330                 335

Met Tyr Pro Glu Asp Gly Ala Leu Lys Ser Glu Ile Lys Lys Gly Leu
            340                 345                 350

Arg Leu Lys Asp Gly Gly His Tyr Ala Ala Glu Val Lys Thr Thr Tyr
        355                 360                 365

Lys Ala Lys Lys Pro Val Gln Leu Pro Gly Ala Tyr Val Val Asp Ile
    370                 375                 380

Lys Leu Asp Ile Val Ser His Asn Glu Asp Tyr Thr Ile Val Glu Gln
385                 390                 395                 400

Cys Glu Arg Ala Glu Gly Arg His Ser Thr Gly Gly Met Val Gly Leu
                405                 410                 415

Tyr Lys


<210> SEQ ID NO 7
<211> LENGTH: 1254
<212> TYPE: DNA
<213> ORGANISM: Homo sapiens

<400> SEQUENCE: 7

atggggagtc tggtgagcaa gggcgaggag gataacatgg ccatcatcaa ggagttcatg     60

cgcttcaagg tgcacatgga gggctccgtg aacggccacg agttcgagat cgagggcgag    120

ggcgagggcc gcccctacga ggcctttcag accgctaagc tgaaggtgac caagggtggc    180

cccctgccct tcgcctggga catcctgtcc cctcagttca tgtacggctc caaggcctac    240

attaagcacc cagccgacat ccccgactac ttcaagctgt ccttccccga gggcttcagg    300

tgggagcgcg tgatgaactt cgaggacggc ggcattattc acgttaacca ggactcctcc    360

ctgcaggacg gcgtattcat ctacaaggtg aagctgcgcg gcaccaactt cccccccgac    420

ggccccgtaa tgcagaagaa gaccatgggc tgggaggcta cgcgcgacca actgactgaa    480

gagcagatcg cagaatttaa agaggctttc tccctatttg acaaggacgg ggatgggacg    540

atgacaacca aggagctggg gacggtgatg cggtctctgg ggcagaaccc cacagaagca    600

gagctgcagg acatgatcag tgaagtagat gccgacggtg acggcacatt cgacttccct    660

gagttcctga cgatgatggc aagaaaaatg aattacacag acagtgaaga ggaaattaga    720

gaagcgttcc gcgtggcgga taaggacggc aatggctaca tcggcgcagc agagcttcgc    780
```

```
cacgcgatga cagacattgg agagaagtta acagatgagg aggttgatga aatgatcagg    840

gtagcagaca tcgatgggga tggtcaggta aactacgaag agtttgtaca aatgatgaca    900

gcgaagggtg gcggaggttc tgtcgactca tcacgtcgta agtggaataa ggcaggtcac    960

gcatggagag ctataggtcg gctgagctca cccgtggttt ccgagcggat gtaccccgag   1020

gacggagccc tgaagagcga gatcaagaag gggctgaggc tgaaggacgg cggccactac   1080

gccgccgagg tcaagaccac ctacaaggcc aagaagcccg tgcagctgcc cggcgcctac   1140

gtcgtcgaca tcaagttgga catcgtgtcc cacaacgagg actacaccat cgtggaacag   1200

tgcgaacgcg ccgagggccg ccactccacc ggcggcatgg tcgggctgta caag         1254
```

```
<210> SEQ ID NO 8
<211> LENGTH: 418
<212> TYPE: PRT
<213> ORGANISM: Homo sapiens

<400> SEQUENCE: 8

Met Gly Ser Leu Val Ser Lys Gly Glu Glu Asp Asn Met Ala Ile Ile
1               5                   10                  15

Lys Glu Phe Met Arg Phe Lys Val His Met Glu Gly Ser Val Asn Gly
            20                  25                  30

His Glu Phe Glu Ile Glu Gly Glu Gly Glu Gly Arg Pro Tyr Glu Ala
        35                  40                  45

Phe Gln Thr Ala Lys Leu Lys Val Thr Lys Gly Gly Pro Leu Pro Phe
    50                  55                  60

Ala Trp Asp Ile Leu Ser Pro Gln Phe Met Tyr Gly Ser Lys Ala Tyr
65                  70                  75                  80

Ile Lys His Pro Ala Asp Ile Pro Asp Tyr Phe Lys Leu Ser Phe Pro
                85                  90                  95

Glu Gly Phe Arg Trp Glu Arg Val Met Asn Phe Glu Asp Gly Gly Ile
            100                 105                 110

Ile His Val Asn Gln Asp Ser Ser Leu Gln Asp Gly Val Phe Ile Tyr
        115                 120                 125

Lys Val Lys Leu Arg Gly Thr Asn Phe Pro Pro Asp Gly Pro Val Met
    130                 135                 140

Gln Lys Lys Thr Met Gly Trp Glu Ala Thr Arg Asp Gln Leu Thr Glu
145                 150                 155                 160

Glu Gln Ile Ala Glu Phe Lys Glu Ala Phe Ser Leu Phe Asp Lys Asp
                165                 170                 175

Gly Asp Gly Thr Met Thr Thr Lys Glu Leu Gly Thr Val Met Arg Ser
            180                 185                 190

Leu Gly Gln Asn Pro Thr Glu Ala Glu Leu Gln Asp Met Ile Ser Glu
        195                 200                 205

Val Asp Ala Asp Gly Asp Gly Thr Phe Asp Phe Pro Glu Phe Leu Thr
    210                 215                 220

Met Met Ala Arg Lys Met Asn Tyr Thr Asp Ser Glu Glu Glu Ile Arg
225                 230                 235                 240

Glu Ala Phe Arg Val Ala Asp Lys Asp Gly Asn Gly Tyr Ile Gly Ala
                245                 250                 255

Ala Glu Leu Arg His Ala Met Thr Asp Ile Gly Glu Lys Leu Thr Asp
            260                 265                 270

Glu Glu Val Asp Glu Met Ile Arg Val Ala Asp Ile Asp Gly Asp Gly
        275                 280                 285
```

```
Gln Val Asn Tyr Glu Glu Phe Val Gln Met Met Thr Ala Lys Gly Gly
    290                 295                 300

Gly Gly Ser Val Asp Ser Ser Arg Arg Lys Trp Asn Lys Ala Gly His
305                 310                 315                 320

Ala Trp Arg Ala Ile Gly Arg Leu Ser Ser Pro Val Val Ser Glu Arg
                325                 330                 335

Met Tyr Pro Glu Asp Gly Ala Leu Lys Ser Glu Ile Lys Lys Gly Leu
            340                 345                 350

Arg Leu Lys Asp Gly Gly His Tyr Ala Ala Glu Val Lys Thr Thr Tyr
        355                 360                 365

Lys Ala Lys Lys Pro Val Gln Leu Pro Gly Ala Tyr Val Val Asp Ile
    370                 375                 380

Lys Leu Asp Ile Val Ser His Asn Glu Asp Tyr Thr Ile Val Glu Gln
385                 390                 395                 400

Cys Glu Arg Ala Glu Gly Arg His Ser Thr Gly Gly Met Val Gly Leu
                405                 410                 415

Tyr Lys


<210> SEQ ID NO 9
<211> LENGTH: 1254
<212> TYPE: DNA
<213> ORGANISM: Homo sapiens

<400> SEQUENCE: 9

atggggagtc tggtgagcaa gggcgaggag gataacatgg ccatcatcaa ggagttcatg      60

cgcttcaagg tgcacatgga gggctccgtg aacggccacg agttcgagat cgagggcgag     120

ggcgagggcc gcccctacga ggcctttcag accgctaagc tgaaggtgac caagggtggc     180

cccctgccct tcgcctggga catcctgtcc cctcagttca tgtacggctc caaggcctac     240

attaagcacc cagccgacat ccccgactac ttcaagctgt ccttccccga gggcttcagg     300

tgggagcgcg tgatgaactt cgaggacggc ggcattattc acgttaacca ggactcctcc     360

ctgcaggacg gcgtattcat ctacaaggtg aagctgcgcg gcaccaactt cccccccgac     420

ggccccgtaa tgcagaagaa gaccatgggc tgggaggcta cgcgcgacca actgactgaa     480

gagcagatcg cagaatttaa agaggctttc tccctatttg acaaggacgg gaatgggacg     540

atgacaacca aggagctggg gacggtgatg cggtctctgg ggcagaaccc cacagaagca     600

gagctgcagg acatgatcag tgaagtagat gccgacggta acggcacatt cgacttccct     660

gagttcctga cgatgatggc aagaaaaatg aattacacag acagtgaaga ggaaattaga     720

gaagcgttcc gcgtggcgga taaggacggc aatggctaca tcggcgcagc agagcttcgc     780

cacgcgatga cagacattgg agagaagtta acagatgagg aggttgatga aatgatcagg     840

gtagcagaca tcgatgggga tggtcaggta aactacgaag agtttgtaca aatgatgaca     900

gcgaagggtg gcggaggttc tgtcgactca tcacgtcgta agtggaataa ggcaggtcac     960

gcatggagag ctataggtcg gctgagctca cccgtggttt ccgagcggat gtaccccgag    1020

gacggagccc tgaagagcga gatcaagaag gggctgaggc tgaaggacgg cggccactac    1080

gccgccgagg tcaagaccac ctacaaggcc aagaagcccg tgcagctgcc cggcgcctac    1140

gtcgtcgaca tcaagttgga catcgtgtcc cacaacgagg actacaccat cgtggaacag    1200

tgcgaacgcg ccgagggccg ccactccacc ggcggcatgg tcgggctgta caag          1254


<210> SEQ ID NO 10
<211> LENGTH: 418
```

<212> TYPE: PRT
<213> ORGANISM: Homo sapiens

<400> SEQUENCE: 10

Met Gly Ser Leu Val Ser Lys Gly Glu Glu Asp Asn Met Ala Ile Ile
1 5 10 15

Lys Glu Phe Met Arg Phe Lys Val His Met Glu Gly Ser Val Asn Gly
20 25 30

His Glu Phe Glu Ile Glu Gly Glu Gly Glu Gly Arg Pro Tyr Glu Ala
35 40 45

Phe Gln Thr Ala Lys Leu Lys Val Thr Lys Gly Gly Pro Leu Pro Phe
50 55 60

Ala Trp Asp Ile Leu Ser Pro Gln Phe Met Tyr Gly Ser Lys Ala Tyr
65 70 75 80

Ile Lys His Pro Ala Asp Ile Pro Asp Tyr Phe Lys Leu Ser Phe Pro
85 90 95

Glu Gly Phe Arg Trp Glu Arg Val Met Asn Phe Glu Asp Gly Gly Ile
100 105 110

Ile His Val Asn Gln Asp Ser Ser Leu Gln Asp Gly Val Phe Ile Tyr
115 120 125

Lys Val Lys Leu Arg Gly Thr Asn Phe Pro Pro Asp Gly Pro Val Met
130 135 140

Gln Lys Lys Thr Met Gly Trp Glu Ala Thr Arg Asp Gln Leu Thr Glu
145 150 155 160

Glu Gln Ile Ala Glu Phe Lys Glu Ala Phe Ser Leu Phe Asp Lys Asp
165 170 175

Gly Asn Gly Thr Met Thr Thr Lys Glu Leu Gly Thr Val Met Arg Ser
180 185 190

Leu Gly Gln Asn Pro Thr Glu Ala Glu Leu Gln Asp Met Ile Ser Glu
195 200 205

Val Asp Ala Asp Gly Asn Gly Thr Phe Asp Phe Pro Glu Phe Leu Thr
210 215 220

Met Met Ala Arg Lys Met Asn Tyr Thr Asp Ser Glu Glu Glu Ile Arg
225 230 235 240

Glu Ala Phe Arg Val Ala Asp Lys Asp Gly Asn Gly Tyr Ile Gly Ala
245 250 255

Ala Glu Leu Arg His Ala Met Thr Asp Ile Gly Glu Lys Leu Thr Asp
260 265 270

Glu Glu Val Asp Glu Met Ile Arg Val Ala Asp Ile Asp Gly Asp Gly
275 280 285

Gln Val Asn Tyr Glu Glu Phe Val Gln Met Met Thr Ala Lys Gly Gly
290 295 300

Gly Gly Ser Val Asp Ser Ser Arg Arg Lys Trp Asn Lys Ala Gly His
305 310 315 320

Ala Trp Arg Ala Ile Gly Arg Leu Ser Ser Pro Val Val Ser Glu Arg
325 330 335

Met Tyr Pro Glu Asp Gly Ala Leu Lys Ser Glu Ile Lys Lys Gly Leu
340 345 350

Arg Leu Lys Asp Gly Gly His Tyr Ala Ala Glu Val Lys Thr Thr Tyr
355 360 365

Lys Ala Lys Lys Pro Val Gln Leu Pro Gly Ala Tyr Val Val Asp Ile
370 375 380

Lys Leu Asp Ile Val Ser His Asn Glu Asp Tyr Thr Ile Val Glu Gln
385 390 395 400

```
Cys Glu Arg Ala Glu Gly Arg His Ser Thr Gly Gly Met Val Gly Leu
                405                 410                 415

Tyr Lys
```

<210> SEQ ID NO 11
<211> LENGTH: 1245
<212> TYPE: DNA
<213> ORGANISM: Homo sapiens

<400> SEQUENCE: 11

```
atggtgagca agggcgagga ggataacatg gccatcatca aggagttcat gcgcttcaag      60

gtgcacatgg agggctccgt gaacggccac gagttcgaga tcgagggcga gggcgagggc     120

cgcccctacg aggcctttca gaccgctaag ctgaaggtga ccaagggtgg cccccctgccc    180

ttcgcctggg acatcctgtc ccttcagttc atgtacggct ccaaggccta cattaagcac     240

ccagccgaca tccccgacta cttcaagctg tccttccccg agggcttcag gtgggagcgc     300

gtgatgatct tcgaggacgg cggcattatt cacgttaacc aggactcctc cctgcaggac     360

ggcgtattca tctacaaggt gaagctgcgc ggcaccaact tcccccccga cggccccgta     420

atgcagaaga agaccatggg ctgggagcct acgcgtgacc aactgactga agagcagatc     480

gcagagttta aagaggcttt ctccctattt gacaaggacg gggatgggac gatgacaacc     540

aaggagctgg ggacggtgtt gcggtctctg ggcagaacc ccacagaagc agagctgcag     600

gacatgatca atgaagtaga tgccgacggt gacggcacat tcgacttccc tgagttcctg     660

acgatgatgg caaggaaaat gaatgactca gacagtgaag aggaaattag agaagcgttc     720

cgcgtggcgg ataaggacgg caatggctac atcggcgcag cagagcttcg ccacgcgatg     780

acagacattg gagagaagtt aacagatgag gaggttgatg aaatgatcag ggtagcagac     840

atcgatgggg atggtcaggt aaactacgaa gagtttgtac aaatgatgac agcgaagggt     900

ggcggaggtt ctgtcgactc atcacgtcgt aagtggaata aggcaggtca cgcatggaga     960

gctataggtc ggctgagctc acgttgggtt tccgagtgga tgtaccccga ggacggcgcc    1020

ctgaagagcg tgatcaagga ggggttgagg ctgaaggacg gcggccacta cgccgccgag    1080

gtcaggacca cctacaaggc caaaaagccc gtgcagctgc ccggcgccta catcgtcgac    1140

atcaagttgg acatcgtgtc ccacaacgag gactacacca tcgtggaaca gtgcgaacgc    1200

gccgagggcc gccactccac cggcggcatg gacgagctgt acaag                    1245
```

<210> SEQ ID NO 12
<211> LENGTH: 415
<212> TYPE: PRT
<213> ORGANISM: Homo sapiens

<400> SEQUENCE: 12

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Ala Phe Gln Thr
        35                  40                  45

Ala Lys Leu Lys Val Thr Lys Gly Gly Pro Leu Pro Phe Ala Trp Asp
    50                  55                  60

Ile Leu Ser Leu Gln Phe Met Tyr Gly Ser Lys Ala Tyr Ile Lys His
65                  70                  75                  80
```

```
Pro Ala Asp Ile Pro Asp Tyr Phe Lys Leu Ser Phe Pro Glu Gly Phe
                85                  90                  95

Arg Trp Glu Arg Val Met Ile Phe Glu Asp Gly Gly Ile Ile His Val
            100                 105                 110

Asn Gln Asp Ser Ser Leu Gln Asp Gly Val Phe Ile Tyr Lys Val Lys
        115                 120                 125

Leu Arg Gly Thr Asn Phe Pro Pro Asp Gly Pro Val Met Gln Lys Lys
    130                 135                 140

Thr Met Gly Trp Glu Pro Thr Arg Asp Gln Leu Thr Glu Glu Gln Ile
145                 150                 155                 160

Ala Glu Phe Lys Glu Ala Phe Ser Leu Phe Asp Lys Asp Gly Asp Gly
                165                 170                 175

Thr Met Thr Thr Lys Glu Leu Gly Thr Val Leu Arg Ser Leu Gly Gln
            180                 185                 190

Asn Pro Thr Glu Ala Glu Leu Gln Asp Met Ile Asn Glu Val Asp Ala
        195                 200                 205

Asp Gly Asp Gly Thr Phe Asp Phe Pro Glu Phe Leu Thr Met Met Ala
    210                 215                 220

Arg Lys Met Asn Asp Ser Asp Ser Glu Glu Glu Ile Arg Glu Ala Phe
225                 230                 235                 240

Arg Val Ala Asp Lys Asp Gly Asn Gly Tyr Ile Gly Ala Ala Glu Leu
                245                 250                 255

Arg His Ala Met Thr Asp Ile Gly Glu Lys Leu Thr Asp Glu Glu Val
            260                 265                 270

Asp Glu Met Ile Arg Val Ala Asp Ile Asp Gly Asp Gly Gln Val Asn
        275                 280                 285

Tyr Glu Glu Phe Val Gln Met Met Thr Ala Lys Gly Gly Gly Gly Ser
    290                 295                 300

Val Asp Ser Ser Arg Arg Lys Trp Asn Lys Ala Gly His Ala Trp Arg
305                 310                 315                 320

Ala Ile Gly Arg Leu Ser Ser Arg Trp Val Ser Glu Trp Met Tyr Pro
                325                 330                 335

Glu Asp Gly Ala Leu Lys Ser Val Ile Lys Glu Gly Leu Arg Leu Lys
            340                 345                 350

Asp Gly Gly His Tyr Ala Ala Glu Val Arg Thr Thr Tyr Lys Ala Lys
        355                 360                 365

Lys Pro Val Gln Leu Pro Gly Ala Tyr Ile Val Asp Ile Lys Leu Asp
    370                 375                 380

Ile Val Ser His Asn Glu Asp Tyr Thr Ile Val Glu Gln Cys Glu Arg
385                 390                 395                 400

Ala Glu Gly Arg His Ser Thr Gly Gly Met Asp Glu Leu Tyr Lys
                405                 410                 415
```

<210> SEQ ID NO 13
<211> LENGTH: 1245
<212> TYPE: DNA
<213> ORGANISM: Homo sapiens

<400> SEQUENCE: 13

```
atggtgagca agggcgagga ggataacatg gccatcatca aggagttcat gcgcttcaag      60

gtgcacatgg agggctccgt gaacggccac gagttcgaga tcgagggcga gggcgagggc     120

cgcccctacg aggcctttca gaccgctaag ctgaaggtga ccaagggtgg ccccctgccc     180

ttcgcctggg acatcctgtc ccttcagttc atgtacggct ccaaggccta cattaagcac     240
```

```
ccagccgaca tccccgacta cttcaagctg tccttccccg agggcttcag gtgggagcgc    300

gtgatgatct tcgaggacgg cggcattatt cacgttaacc aggactcctc cctgcaggac    360

ggcgtattca tctacaaggt gaagctgcgc ggcaccaact tcccccccga cggccccgta    420

atgcagaaga agaccatggg ctgggagcct acgcgtgacc aactgactga agagcagatc    480

gcagagttta aagaggcttt ctccctattt gacaaggacg ggaatgggac gatgacaacc    540

aaggagctgg ggacggtgtt gcggtctctg ggcagaaccc ccacagaagc agagctgcag    600

gacatgatca atgaagtaga tgccgacggt aacggcacat tcgacttccc tgagttcctg    660

acgatgatgg caaggaaaat gaatgactca gacagtgaag aggaaattag agaagcgttc    720

cgcgtggcgg ataaggacgg caatggctac atcggcgcag cagagcttcg ccacgcgatg    780

acagacattg gagagaagtt aacagatgag gaggttgatg aaatgatcag ggtagcagac    840

atcgatgggg atggtcaggt aaactacgaa gagtttgtac aaatgatgac agcgaagggt    900

ggcggaggtt ctgtcgactc atcacgtcgt aagtggaata aggcaggtca cgcatggaga    960

gctataggtc ggctgagctc acgttgggtt tccgagtgga tgtaccccga ggacggcgcc   1020

ctgaagagcg tgatcaagga ggggttgagg ctgaaggacg gcggccacta cgccgccgag   1080

gtcaggacca cctacaaggc caaaaagccc gtgcagctgc ccggcgccta catcgtcgac   1140

atcaagttgg acatcgtgtc ccacaacgag gactacacca tcgtggaaca gtgcgaacgc   1200

gccgagggcc gccactccac cggcggcatg gacgagctgt acaag                   1245
```

```
<210> SEQ ID NO 14
<211> LENGTH: 415
<212> TYPE: PRT
<213> ORGANISM: Homo sapiens

<400> SEQUENCE: 14

Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Ala Phe Gln Thr
        35                  40                  45

Ala Lys Leu Lys Val Thr Lys Gly Gly Pro Leu Pro Phe Ala Trp Asp
    50                  55                  60

Ile Leu Ser Leu Gln Phe Met Tyr Gly Ser Lys Ala Tyr Ile Lys His
65                  70                  75                  80

Pro Ala Asp Ile Pro Asp Tyr Phe Lys Leu Ser Phe Pro Glu Gly Phe
                85                  90                  95

Arg Trp Glu Arg Val Met Ile Phe Glu Asp Gly Gly Ile Ile His Val
            100                 105                 110

Asn Gln Asp Ser Ser Leu Gln Asp Gly Val Phe Ile Tyr Lys Val Lys
        115                 120                 125

Leu Arg Gly Thr Asn Phe Pro Pro Asp Gly Pro Val Met Gln Lys Lys
    130                 135                 140

Thr Met Gly Trp Glu Pro Thr Arg Asp Gln Leu Thr Glu Glu Gln Ile
145                 150                 155                 160

Ala Glu Phe Lys Glu Ala Phe Ser Leu Phe Asp Lys Asp Gly Asn Gly
                165                 170                 175

Thr Met Thr Thr Lys Glu Leu Gly Thr Val Leu Arg Ser Leu Gly Gln
            180                 185                 190

Asn Pro Thr Glu Ala Glu Leu Gln Asp Met Ile Asn Glu Val Asp Ala
```

```
        195                 200                 205

Asp Gly Asn Gly Thr Phe Asp Phe Pro Glu Phe Leu Thr Met Met Ala
    210                 215                 220

Arg Lys Met Asn Asp Ser Asp Ser Glu Glu Glu Ile Arg Glu Ala Phe
225                 230                 235                 240

Arg Val Ala Asp Lys Asp Gly Asn Gly Tyr Ile Gly Ala Ala Glu Leu
                245                 250                 255

Arg His Ala Met Thr Asp Ile Gly Glu Lys Leu Thr Asp Glu Glu Val
            260                 265                 270

Asp Glu Met Ile Arg Val Ala Asp Ile Asp Gly Asp Gly Gln Val Asn
        275                 280                 285

Tyr Glu Glu Phe Val Gln Met Met Thr Ala Lys Gly Gly Gly Gly Ser
    290                 295                 300

Val Asp Ser Ser Arg Arg Lys Trp Asn Lys Ala Gly His Ala Trp Arg
305                 310                 315                 320

Ala Ile Gly Arg Leu Ser Ser Arg Trp Val Ser Glu Trp Met Tyr Pro
                325                 330                 335

Glu Asp Gly Ala Leu Lys Ser Val Ile Lys Glu Gly Leu Arg Leu Lys
            340                 345                 350

Asp Gly Gly His Tyr Ala Ala Glu Val Arg Thr Thr Tyr Lys Ala Lys
        355                 360                 365

Lys Pro Val Gln Leu Pro Gly Ala Tyr Ile Val Asp Ile Lys Leu Asp
    370                 375                 380

Ile Val Ser His Asn Glu Asp Tyr Thr Ile Val Glu Gln Cys Glu Arg
385                 390                 395                 400

Ala Glu Gly Arg His Ser Thr Gly Gly Met Asp Glu Leu Tyr Lys
                405                 410                 415
```

<210> SEQ ID NO 15
<211> LENGTH: 1251
<212> TYPE: DNA
<213> ORGANISM: Homo sapiens

<400> SEQUENCE: 15

```
atggttgact cttcacgtcg taagtggaat aaggcaggtc acgcagtcag agctataggt     60

cggctgagct cacgttgggt ttccgagtgg atgtaccccg aggacggcgc cctgaagagc    120

gtgatcaagg aggggttgag gctgaaggac ggcggccact acgccgccga ggtcaggacc    180

acctacaagg ccaaaaagcc cgtgcagctg cccggcgcct acatcgtcga catcaagttg    240

gacatcgtgt cccacaacga ggactacacc atcgtggaac agtgcgaacg cgccgagggc    300

cgccacccca ccggcggcat ggtcgggctg tacaagggag gtacaggcgg gagtctggtg    360

agcaagggcg aggaggataa catggccatc atcaaggagt tcatgcgctt caaggtgcac    420

atggagggct ccgtgaacgg ccacgagttc gagatcgagg gcgagggcga gggccgcccc    480

tacgaggcct ttcagaccgc taagctgaag gtgaccaagg gtggccccct gcccttcgcc    540

tgggacatcc tgtcccttca gttcatgtac ggctccaagg cctacattaa gcacccagcc    600

gacatccccg actacttcaa gctgtccttc cccgagggct tcaggtggga gcgcgtgatg    660

atcttcgagg acggcggcat tattcacgtt aaccaggact cctccctgca ggacggcgta    720

ttcatctaca aggtgaagct gcgcggcacc aacttccccc ccgacggccc cgtaatgcag    780

aagaagacca tgggctggga gcctacgcgt gaccaactga ctgaagagca gatcgcagaa    840

tttaaagagg ctttctccct atttgacaag gacggggatg ggacaataac aaccaaggat    900
```

```
ctggggacgg tgctgcggtc tctggggcag aaccccacag aagcagagct ccaggacatg    960

atcaatgaag tagatgccga cggtaatggc acaatcgact tccctgattt cctgacaatg   1020

atggcaagaa aaatgaaaga cacagacagt gaagaagaaa ttcgcgaagc gttccgtgtg   1080

tgggataagg atggcaatgg ctacatctct gcagcagacc ttcgccacgt gatgacaaac   1140

cttggagaga agttaacaga tgaagaggtt gatgaaatga tcagggaagc agatatcgat   1200

ggagaaggtc aggtaaacta cgaagagttt gtacaaatga tgacagcgaa g            1251


<210> SEQ ID NO 16
<211> LENGTH: 417
<212> TYPE: PRT
<213> ORGANISM: Homo sapiens

<400> SEQUENCE: 16

Met Val Asp Ser Ser Arg Arg Lys Trp Asn Lys Ala Gly His Ala Val
1               5                   10                  15

Arg Ala Ile Gly Arg Leu Ser Ser Arg Trp Val Ser Glu Trp Met Tyr
            20                  25                  30

Pro Glu Asp Gly Ala Leu Lys Ser Val Ile Lys Glu Gly Leu Arg Leu
        35                  40                  45

Lys Asp Gly Gly His Tyr Ala Ala Glu Val Arg Thr Thr Tyr Lys Ala
    50                  55                  60

Lys Lys Pro Val Gln Leu Pro Gly Ala Tyr Ile Val Asp Ile Lys Leu
65                  70                  75                  80

Asp Ile Val Ser His Asn Glu Asp Tyr Thr Ile Val Glu Gln Cys Glu
                85                  90                  95

Arg Ala Glu Gly Arg His Pro Thr Gly Gly Met Val Gly Leu Tyr Lys
            100                 105                 110

Gly Gly Thr Gly Gly Ser Leu Val Ser Lys Gly Glu Glu Asp Asn Met
        115                 120                 125

Ala Ile Ile Lys Glu Phe Met Arg Phe Lys Val His Met Glu Gly Ser
    130                 135                 140

Val Asn Gly His Glu Phe Glu Ile Glu Gly Glu Gly Glu Gly Arg Pro
145                 150                 155                 160

Tyr Glu Ala Phe Gln Thr Ala Lys Leu Lys Val Thr Lys Gly Gly Pro
                165                 170                 175

Leu Pro Phe Ala Trp Asp Ile Leu Ser Leu Gln Phe Met Tyr Gly Ser
            180                 185                 190

Lys Ala Tyr Ile Lys His Pro Ala Asp Ile Pro Asp Tyr Phe Lys Leu
        195                 200                 205

Ser Phe Pro Glu Gly Phe Arg Trp Glu Arg Val Met Ile Phe Glu Asp
    210                 215                 220

Gly Gly Ile Ile His Val Asn Gln Asp Ser Ser Leu Gln Asp Gly Val
225                 230                 235                 240

Phe Ile Tyr Lys Val Lys Leu Arg Gly Thr Asn Phe Pro Pro Asp Gly
                245                 250                 255

Pro Val Met Gln Lys Lys Thr Met Gly Trp Glu Pro Thr Arg Asp Gln
            260                 265                 270

Leu Thr Glu Glu Gln Ile Ala Glu Phe Lys Glu Ala Phe Ser Leu Phe
        275                 280                 285

Asp Lys Asp Gly Asp Gly Thr Ile Thr Thr Lys Asp Leu Gly Thr Val
    290                 295                 300

Leu Arg Ser Leu Gly Gln Asn Pro Thr Glu Ala Glu Leu Gln Asp Met
305                 310                 315                 320
```

```
Ile Asn Glu Val Asp Ala Asp Gly Asn Gly Thr Ile Asp Phe Pro Asp
                325                 330                 335

Phe Leu Thr Met Met Ala Arg Lys Met Lys Asp Thr Asp Ser Glu Glu
            340                 345                 350

Glu Ile Arg Glu Ala Phe Arg Val Trp Asp Lys Asp Gly Asn Gly Tyr
        355                 360                 365

Ile Ser Ala Ala Asp Leu Arg His Val Met Thr Asn Leu Gly Glu Lys
    370                 375                 380

Leu Thr Asp Glu Glu Val Asp Glu Met Ile Arg Glu Ala Asp Ile Asp
385                 390                 395                 400

Gly Glu Gly Gln Val Asn Tyr Glu Glu Phe Val Gln Met Met Thr Ala
                405                 410                 415

Lys


<210> SEQ ID NO 17
<211> LENGTH: 1245
<212> TYPE: DNA
<213> ORGANISM: Homo sapiens

<400> SEQUENCE: 17

atggtgagca agggcgagga ggataacatg gccatcatca aggagttcat gcgcttcaag      60

gtgcacatgg agggctccgt gaacggccac gagttcgaga tcgagggcga gggcgagggc     120

cgcccctacg aggcctttca gaccgctaag ctgaaggtga ccaagggtgg cccccctgccc    180

ttcgcctggg acatcctgtc ccttcagttc atgtacggct ccaaggccta cattaagcac     240

ccagccgaca tccccgacta cttcaagctg tccttccccg agggcttcag gtgggagcgc     300

gtgatgatct tcgaggacgg cggcattatt cacgttaacc aggactcctc cctgcaggac     360

ggcgtattca tctacaaggt gaagctgcgc ggcaccaact tcccccccga cggccccgta     420

atgcagaaga agaccatggg ctgggagcct actcgggacc aactgactga agagcagatc     480

gcagaattta aagaggcttt ctccctattt gacaaggacg gggatgggac aataacaacc     540

aaggatctgg ggacggtgct gcggtctctg gggcagaacc ccacagaagc agagctccag     600

gacatgatca atgaagtaga tgccgacggt aatggcacaa tcgacttccc tgatttcctg     660

acaatgatgg caagaaaaat gaaagacaca gacagtgaag aagaaattcg cgaagcgttc     720

cgtgtgtggg ataaggatgg caatggctac atctctgcag cagaccttcg ccacgtgatg     780

acaaaccttg gagagaagtt aacagatgaa gaggttgatg aaatgatcag ggaagcagat     840

atcgatggag aaggtcaggt aaactacgaa gagtttgtac aaatgatgac agcgaagggt     900

ggcggaggtt ctgtcgactc atcacgtcgt aagtggaata aggcaggtca cgcagtcaga     960

gctataggtc ggctgagctc acgttgggtt tccgagtgga tgtaccccga ggacggcgcc    1020

ctgaagagcg tgatcaagga ggggttgagg ctgaaggacg gcggccacta cgccgccgag    1080

gtcaggacca cctacaaggc caaaaagccc gtgcagctgc ccggcgccta catcgtcgac    1140

atcaagttgg acatcgtgtc ccacaacgag gactacacca tcgtggaaca gtgcgaacgc    1200

gccgagggcc gccactccac cggcggcatg gacgagctgt acaag                    1245


<210> SEQ ID NO 18
<211> LENGTH: 415
<212> TYPE: PRT
<213> ORGANISM: Homo sapiens

<400> SEQUENCE: 18
```

-continued

```
Met Val Ser Lys Gly Glu Glu Asp Asn Met Ala Ile Ile Lys Glu Phe
1               5                   10                  15

Met Arg Phe Lys Val His Met Glu Gly Ser Val Asn Gly His Glu Phe
            20                  25                  30

Glu Ile Glu Gly Glu Gly Glu Gly Arg Pro Tyr Glu Ala Phe Gln Thr
        35                  40                  45

Ala Lys Leu Lys Val Thr Lys Gly Gly Pro Leu Pro Phe Ala Trp Asp
    50                  55                  60

Ile Leu Ser Leu Gln Phe Met Tyr Gly Ser Lys Ala Tyr Ile Lys His
65                  70                  75                  80

Pro Ala Asp Ile Pro Asp Tyr Phe Lys Leu Ser Phe Pro Glu Gly Phe
                85                  90                  95

Arg Trp Glu Arg Val Met Ile Phe Glu Asp Gly Gly Ile Ile His Val
            100                 105                 110

Asn Gln Asp Ser Ser Leu Gln Asp Gly Val Phe Ile Tyr Lys Val Lys
        115                 120                 125

Leu Arg Gly Thr Asn Phe Pro Pro Asp Gly Pro Val Met Gln Lys Lys
    130                 135                 140

Thr Met Gly Trp Glu Pro Thr Arg Asp Gln Leu Thr Glu Glu Gln Ile
145                 150                 155                 160

Ala Glu Phe Lys Glu Ala Phe Ser Leu Phe Asp Lys Asp Gly Asp Gly
                165                 170                 175

Thr Ile Thr Thr Lys Asp Leu Gly Thr Val Leu Arg Ser Leu Gly Gln
            180                 185                 190

Asn Pro Thr Glu Ala Glu Leu Gln Asp Met Ile Asn Glu Val Asp Ala
        195                 200                 205

Asp Gly Asn Gly Thr Ile Asp Phe Pro Asp Phe Leu Thr Met Met Ala
    210                 215                 220

Arg Lys Met Lys Asp Thr Asp Ser Glu Glu Glu Ile Arg Glu Ala Phe
225                 230                 235                 240

Arg Val Trp Asp Lys Asp Gly Asn Gly Tyr Ile Ser Ala Ala Asp Leu
                245                 250                 255

Arg His Val Met Thr Asn Leu Gly Glu Lys Leu Thr Asp Glu Glu Val
            260                 265                 270

Asp Glu Met Ile Arg Glu Ala Asp Ile Asp Gly Glu Gly Gln Val Asn
        275                 280                 285

Tyr Glu Glu Phe Val Gln Met Met Thr Ala Lys Gly Gly Gly Gly Ser
    290                 295                 300

Val Asp Ser Ser Arg Arg Lys Trp Asn Lys Ala Gly His Ala Val Arg
305                 310                 315                 320

Ala Ile Gly Arg Leu Ser Ser Arg Trp Val Ser Glu Trp Met Tyr Pro
                325                 330                 335

Glu Asp Gly Ala Leu Lys Ser Val Ile Lys Glu Gly Leu Arg Leu Lys
            340                 345                 350

Asp Gly Gly His Tyr Ala Ala Glu Val Arg Thr Thr Tyr Lys Ala Lys
        355                 360                 365

Lys Pro Val Gln Leu Pro Gly Ala Tyr Ile Val Asp Ile Lys Leu Asp
    370                 375                 380

Ile Val Ser His Asn Glu Asp Tyr Thr Ile Val Glu Gln Cys Glu Arg
385                 390                 395                 400

Ala Glu Gly Arg His Ser Thr Gly Gly Met Asp Glu Leu Tyr Lys
                405                 410                 415
```

```
<210> SEQ ID NO 19
<211> LENGTH: 17
<212> TYPE: PRT
<213> ORGANISM: Homo sapiens

<400> SEQUENCE: 19

Met Leu Leu Pro Val Pro Leu Leu Leu Gly Leu Leu Gly Ala Ala Ala
1               5                   10                  15

Asp


<210> SEQ ID NO 20
<211> LENGTH: 38
<212> TYPE: DNA
<213> ORGANISM: Homo sapiens

<400> SEQUENCE: 20

gatcggatcc aaccatggtg agcaagggcg aggaggat                          38


<210> SEQ ID NO 21
<211> LENGTH: 34
<212> TYPE: DNA
<213> ORGANISM: Homo sapiens

<400> SEQUENCE: 21

gatcaagctt ttacttgtac agctcgtcca tgcc                              34
```